US 10,825,178 B1

United States Patent
Jeong et al.

(10) Patent No.: US 10,825,178 B1
(45) Date of Patent: Nov. 3, 2020

(54) APPARATUS FOR QUALITY MANAGEMENT OF MEDICAL IMAGE INTERPRETATION USING MACHINE LEARNING, AND METHOD THEREOF

(71) Applicant: Lunit Inc., Seoul (KR)

(72) Inventors: Nayoung Jeong, Seoul (KR); Ki Hwan Kim, Seoul (KR); Minhong Jang, Seoul (KR)

(73) Assignee: Lunit Inc., Seoul (KR)

( * ) Notice: Subject to any disclaimer, the term of this patent is extended or adjusted under 35 U.S.C. 154(b) by 0 days.

(21) Appl. No.: 16/707,830

(22) Filed: Dec. 9, 2019

(30) Foreign Application Priority Data

Sep. 5, 2019 (KR) .................. 10-2019-0109855

(51) Int. Cl.
*G06T 7/00* (2017.01)
*G16H 30/20* (2018.01)
(Continued)

(52) U.S. Cl.
CPC ......... *G06T 7/0014* (2013.01); *G06N 3/0454* (2013.01); *G06N 3/08* (2013.01);
(Continued)

(58) Field of Classification Search
CPC ......... G06T 7/0014; G06T 2207/20081; G06T 2207/30004; G16H 30/20; G16H 30/40; G06N 20/00; G06N 3/0454; G06N 3/08
See application file for complete search history.

(56) References Cited

U.S. PATENT DOCUMENTS

2016/0364862 A1* 12/2016 Reicher ............... A61B 5/7267
2019/0131016 A1* 5/2019 Cohen ................. G06K 9/6274
(Continued)

FOREIGN PATENT DOCUMENTS

JP          05-012351 A      1/1993
KR      10-1811028 B1     12/2017
(Continued)

OTHER PUBLICATIONS

Office Action of corresponding Korean Patent Application No. 10-2019-0109855 with English Translation—11 pages (dated Nov. 18, 2019).
(Continued)

*Primary Examiner* — Kamran Afshar
*Assistant Examiner* — Marshall L Werner
(74) *Attorney, Agent, or Firm* — Knobbe Martens Olson & Bear LLP

(57) ABSTRACT

Provided are a computerized image interpretation method and a device for analyzing a medical image. The image interpretation method may include receiving, at a processor, a medical image, and receiving report information including a healthcare worker's judgement result of the medical image. The method may also include generating, at the processor, result information representing correspondence between first lesion information, which is related to a lesion in the medical image acquired on the basis of the medical image, and second lesion information, which is related to a lesion in the medical image acquired on the basis of the report information, by applying the first lesion information and the second lesion information to a third analysis model. The method may further include outputting, at the processor, the result information.

12 Claims, 13 Drawing Sheets

(51) Int. Cl.
  *G16H 30/40*    (2018.01)
  *G06N 3/04*     (2006.01)
  *G06N 3/08*     (2006.01)
  *G06N 20/00*    (2019.01)

(52) U.S. Cl.
  CPC ............ *G06N 20/00* (2019.01); *G16H 30/20* (2018.01); *G16H 30/40* (2018.01); *G06T 2207/20081* (2013.01); *G06T 2207/30004* (2013.01)

(56) References Cited

U.S. PATENT DOCUMENTS

| | | | |
|---|---|---|---|
| 2019/0188870 A1* | 6/2019 | Park ............ | G06T 7/30 |
| 2019/0295248 A1* | 9/2019 | Nakamura ............ | G16H 30/40 |
| 2020/0160993 A1* | 5/2020 | Xie ............ | G06F 40/20 |
| 2020/0176112 A1* | 6/2020 | Sati ............ | G16H 50/20 |

FOREIGN PATENT DOCUMENTS

| | | |
|---|---|---|
| KR | 10-2018-0040287 A | 4/2018 |
| KR | 10-2019-0102399 A | 9/2019 |

OTHER PUBLICATIONS

Office Action of corresponding Korean Patent Application No. 10-2019-0109855 with English Translation—5 pages (dated Mar. 30, 2020).

\* cited by examiner

APPARATUS FOR QUALITY MANAGEMENT OF MEDICAL IMAGE INTERPRETATION USING MACHINE LEARNING, AND METHOD THEREOF

CROSS-REFERENCE TO RELATED APPLICATION

This application claims priority to and the benefit of Korean Patent Application No. 2019-0109855, filed on Sep. 5, 2019, the disclosure of which is incorporated herein by reference in its entirety.

BACKGROUND

1. Technical Field

The present disclosure relates to a computerized image interpretation method and a device for analyzing a medical image and more particularly, to a medical image analysis device and method for managing medical image interpretation results by comparing an interpretation result of a medical image made by a healthcare worker with an interpretation result generated on the basis of a machine learning model.

2. Discussion of Related Technology

An imaging examination is used to detect a new disease or observe a change in an existing lesion. Imaging examination is important as the beginning of patient diagnosis.

However, due to the aging population, an increase in private health insurance participation rate, the expansion of medical care expenses, etc., the number of imaging examinations carried out is rapidly increasing, and the interpretation load of medical imaging specialists is increasing accordingly. Also, the accuracy of a medical image interpretation may vary depending on various factors, such as an interpretation environment, a detailed specialty of a healthcare worker, and the healthcare worker's concentration. Therefore, healthcare workers are likely to put wrong interpretations on medical images and may put different interpretations on the same medical image.

Actually, in some cases, treatment may be delayed because a healthcare worker cannot interpret a lesion in a medical image, or a wrong drug prescription may be given or a wrong operation may be carried out because a healthcare worker interprets a lesion shown in a medical image as another lesion.

SUMMARY

There is an increasing necessity to manage the quality of medical image interpretations. Methods of managing the quality of medical image interpretations may be classified into two types. The first type is a method of educating healthcare workers. Since medical images are interpreted by healthcare workers, it is possible to improve the quality of medical image interpretations by educating healthcare workers regularly and having healthcare workers take a test.

According to this method, however, it is difficult to evaluate the accuracy of an interpretation in an actual clinical environment. Also, it is not possible to take measures against an image which was interpreted wrongly in the past.

The second type is a duplicate interpretation. In this method, a medical image which has already been interpreted by a healthcare worker is interpreted again by another healthcare worker. According to this method, a medical image is interpreted by different healthcare workers, and thus it is possible to prevent an interpretation error of one healthcare worker. However, since the number of medical imaging workers is limited, this method is unlikely to be implemented in practice.

Consequently, a device and method are required for managing the quality of medical image interpretations.

According to an aspect of the present disclosure, there is provided an image interpretation method including receiving a medical image, receiving report information which is a healthcare worker's judgement result of the medical image, generating result information representing correspondence between first lesion information and second lesion information by applying the first lesion information, which is related to a lesion in the medical image acquired on the basis of the medical image, and the second lesion information, which is related to a lesion in the medical image acquired on the basis of the report information, to a third analysis model, and outputting the result information.

The first lesion information (data) may include at least one of the medical image, first lesion presence information (data) representing whether there is a lesion in the medical image, first lesion area information including a location of a lesion in the medical image and a size of the lesion, and first report information automatically generated from the medical image by a first analysis model.

The first lesion information may include first feature information about at least one feature related to a hidden layer of the first analysis model for generating the first lesion presence information from the medical image.

The second lesion information may include at least one of the report information, second lesion presence information representing whether there is a lesion acquired on the basis of the report information, and second lesion area information including a location of a lesion acquired on the basis of the report information and a size of the lesion.

The second lesion information may include second feature information about at least one feature related to a hidden layer of a second analysis model for generating the second lesion presence information from the report information.

The method may further include acquiring the first lesion information by applying the medical image to a first analysis model, and acquiring the second lesion information by applying the report information to a second analysis model. The first analysis model may be a model which has machine-learned correlations between a plurality of past medical images and a plurality of pieces of first past lesion information about the plurality of past medical images, the second analysis model may include a model which has machine-learned correlations between a plurality of pieces of past report information and a plurality of pieces of second past lesion information about the plurality of pieces of past report information, and the third analysis model may be a model which has machine-learned the plurality of pieces of first past lesion information, the plurality of pieces of second past lesion information, and past result information representing correspondence between the plurality of pieces of first past lesion information and the plurality of pieces of second past lesion information.

The second analysis model may be a rule-based model for extracting the second lesion information from the report information.

The generating of the result information may include determining the result information on the basis of whether first lesion presence information included in the first lesion information and second lesion presence information included in the second lesion information coincide with each other.

The generating of the result information may include generating the result information on the basis of the degree of regional coincidence between lesion areas based on first lesion area information included in the first lesion information and second lesion area information included in the second lesion information.

The generating of the result information may include generating the result information by applying first feature information (data) included in the first lesion information and second feature information (data) included in the second lesion information to the third analysis model which is a machine learning model.

The generating of the result information may include generating the result information by applying first report information, which is generated as a report from the first lesion information, and the report information to the third analysis model which is a machine learning model.

The generating of the result information may include generating the result information by applying the medical image and second lesion area information included in the second lesion information to the third analysis model which is a machine learning model.

According to another aspect of the present disclosure, there is provided a device for analyzing a medical image, the device including a processor and a memory. On the basis of instructions stored in the memory, the processor performs operations of receiving a medical image, receiving report information which is a healthcare worker's judgement result of the medical image, generating result information representing correspondence between first lesion information and second lesion information by applying the first lesion information, which is related to a lesion in the medical image acquired on the basis of the medical image, and the second lesion information, which is related to a lesion in the medical image acquired on the basis of the report information, to a third analysis model, and outputting the result information.

The first lesion information may include at least one of the medical image, first lesion presence information representing whether there is a lesion in the medical image, first lesion area information including a location of a lesion in the medical image and a size of the lesion, and first report information automatically generated from the medical image by a first analysis model.

The first lesion information may include first feature information about at least one feature related to a hidden layer of the first analysis model for generating the first lesion presence information from the medical image.

The second lesion information may include at least one of the report information, second lesion presence information representing whether there is a lesion acquired on the basis of the report information, and second lesion area information including a location of a lesion acquired on the basis of the report information and a size of the lesion.

The second lesion information may include second feature information about at least one feature related to a hidden layer of a second analysis model for generating the second lesion presence information from the report information.

On the basis of the instructions stored in the memory, the processor may further perform operations of acquiring the first lesion information by applying the medical image to a first analysis model, and acquiring the second lesion information by applying the report information to a second analysis model. The first analysis model may be a model which has machine-learned correlations between a plurality of past medical images and a plurality of pieces of first past lesion information about the plurality of past medical images, the second analysis model may include a model which has machine-learned correlations between a plurality of pieces of past report information and a plurality of pieces of second past lesion information about the plurality of pieces of past report information, and the third analysis model may be a model which has machine-learned the plurality of pieces of first past lesion information, the plurality of pieces of second past lesion information, and past result information representing correspondence between the plurality of pieces of first past lesion information and the plurality of pieces of second past lesion information.

The second analysis model may be a rule-based model for extracting the second lesion information from the report information.

On the basis of the instructions stored in the memory, the processor may perform an operation of determining the result information on the basis of whether first lesion presence information included in the first lesion information and second lesion presence information included in the second lesion information coincide with each other.

On the basis of the instructions stored in the memory, the processor may perform an operation of generating the result information on the basis of the degree of regional coincidence between lesion areas based on first lesion area information included in the first lesion information and second lesion area information included in the second lesion information.

On the basis of the instructions stored in the memory, the processor may perform an operation of generating the result information by applying first feature information included in the first lesion information and second feature information included in the second lesion information to the third analysis model which is a machine learning model.

On the basis of the instructions stored in the memory, the processor may perform an operation of generating the result information by applying first report information, which is generated as a report from the first lesion information, and the report information to the third analysis model which is a machine learning model.

On the basis of the instructions stored in the memory, the processor may perform an operation of generating the result information by applying the medical image and second lesion area information included in the second lesion information to the third analysis model which is a machine learning model.

According to another aspect of the present disclosure, there is provided a program for implementing the above-described image interpretation method, the program being recorded in a computer-readable recording medium.

BRIEF DESCRIPTION OF THE DRAWINGS

The above and other objects, features and advantages of the present disclosure will become more apparent to those of ordinary skill in the art by describing in detail embodiments thereof with reference to the accompanying drawings.

DETAILED DESCRIPTION OF EMBODIMENTS

Figure 1:
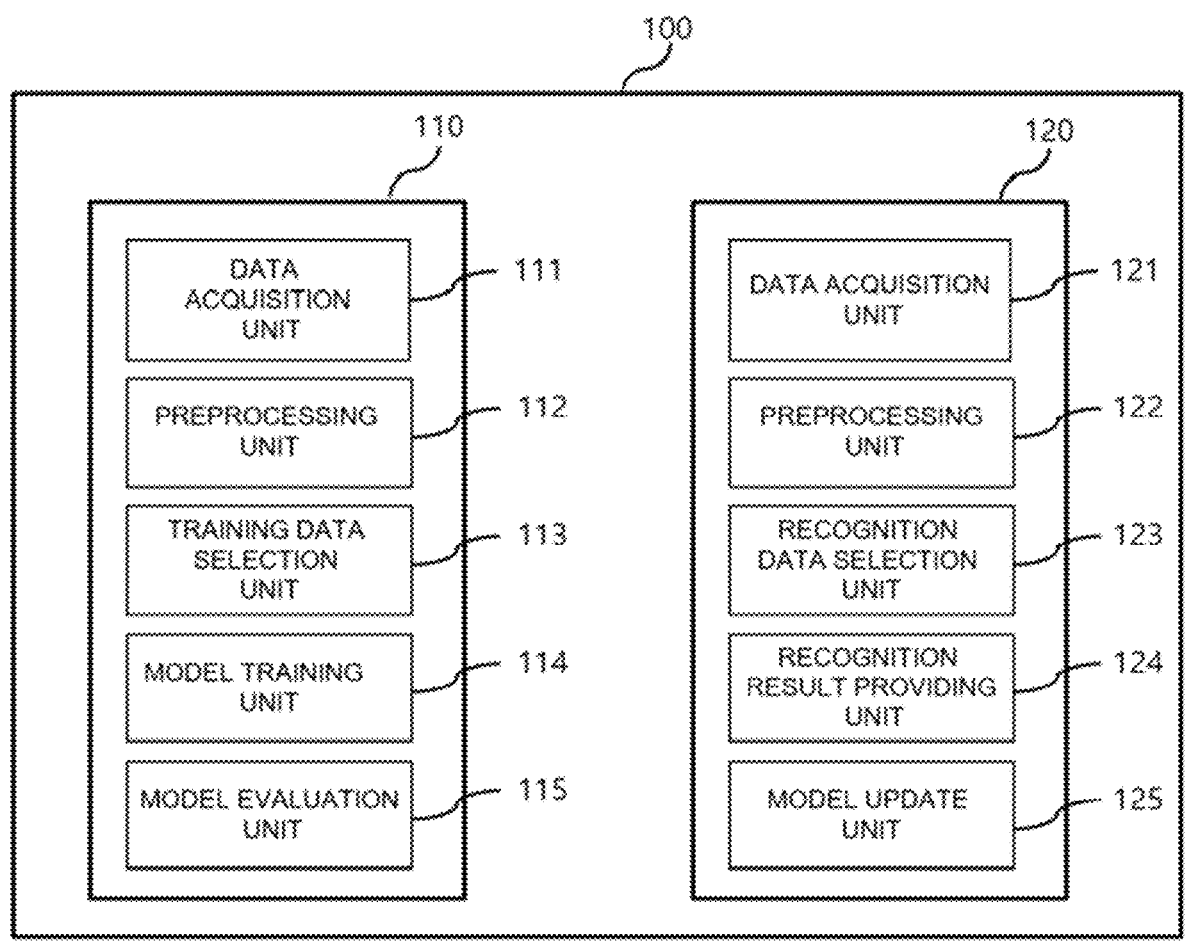
FIG. 1 is a block diagram of a medical image analysis device according to an embodiment of the present disclosure.

Advantages and features of the present disclosure and methods for achieving them will be made clear from embodiments described below with reference to the accompanying drawings. However, the present disclosure may be embodied in many different forms and should not be construed as being limited to the embodiments set forth herein. Rather, these embodiments are provided so that this disclosure will be thorough and complete and will fully convey the scope of the present disclosure to those of ordinary skill in the technical field to which the present disclosure pertains.

Terms used herein will be described in brief, and then disclosed embodiments will be described in detail.

Although the terms used herein are selected from among general terms that are currently and widely used in consideration of functions in the present disclosure, these may be changed according to intentions of those of ordinary skill in the art, precedents, the advent of new technology, and the like. In addition, in specific cases, some terms may be arbitrarily selected by applicants. In this case, meanings thereof will be described in detail in a corresponding description of this disclosure. Therefore, the terms used herein should defined on the basis of meanings of the terms and overall content of this disclosure rather than simply the terms themselves.

As used herein, the singular forms include the plural forms as well unless clearly indicated otherwise by context. Likewise, the plural forms include the singular forms as well unless clearly indicated otherwise by context.

Throughout the specification, when a part is referred to as "including" an element, unless particularly defined otherwise, the part does not exclude other elements and may further include other elements.

As used herein, the term "unit" refers to a software or hardware element, and a "unit" performs some roles. However, the term "unit" is not limited to hardware or software. A "unit" may be configured to reside in an addressable storage medium or to execute one or more processors. Therefore, as an example, "units" include elements, such as software elements, object-oriented software elements, class elements, and task elements, processes, functions, attributes, procedures, subroutines, program code segments, drivers, firmware, microcode, circuits, data, databases, data structures, tables, arrays, and variables. Functions provided by elements and "units" may be combined into a smaller number of elements and "units" or may be subdivided into additional elements and "units."

According to an embodiment of the present disclosure, a "unit" may be implemented by a processor and a memory. The term "processor" should be broadly construed as including a general purpose processor, a central processing unit (CPU), a microprocessor, a digital signal processor (DSP), a controller, a microcontroller, a state machine, and the like. In some circumstances, a "processor" may refer to an application-specific integrated circuit (ASIC), a programmable logic device (PLD), a field programmable gate array (FPGA), and the like. The term "processor" may refer to a combination of processing devices, such as a combination of a DSP and a microprocessor, a combination of a plurality of microprocessors, a combination of one or more microprocessors combined with a DSP core, or any other combination of such elements.

The term "memory" should be broadly construed as including any electronic component capable of storing electronic information. The term "memory" may refer to various types of processor-readable media, such as a random access memory (RAM), a read-only memory (ROM), a non-volatile random access memory (NVRAM), a programmable read-only memory (PROM), an erasable-programmable read-only memory (EPROM), an electrically erasable PROM (EEPROM), a flash memory, a magnetic or optical data storage device, and a register. While a processor is able to read and/or write information from and/or to a memory, the memory is referred to as in electronic communication with the processor. A memory integrated into a processor is in electronic communication with the processor.

Hereinafter, embodiments of the present disclosure will be described in detail with reference to the accompanying drawings so that those of ordinary skill in the art may readily implement embodiments of the present disclosure. Throughout the drawings, parts irrelevant to the description will be omitted to clearly describe the disclosure.

FIG. 1 is a block diagram of a medical image analysis device 100 according to an embodiment of the present disclosure.

Referring to FIG. 1, the medical image analysis device 100 according to an embodiment of the present disclosure may include a data learning unit 110 and a data recognition unit 120. The aforementioned medical image analysis device 100 may include a processor and a memory.

The data learning unit 110 may train a machine learning model for performing a target task using a data set. The data learning unit 110 may receive the data set and label information related to the target task. The data learning unit 110 may acquire a machine learning model by performing machine learning on a relation between the data set and the label information. As an embodiment, the machine teaming model acquired by the data learning unit 110 may be a model for evaluating the accuracy of a medical image interpretation made by a healthcare worker on the basis of a medical image and report information generated by the healthcare worker.

The data recognition unit 120 may store the machine learning model of the data learning unit 110. The data recognition unit 120 may apply a medical image and report information generated by a healthcare worker to the machine learning model and output information related to the accuracy of the report information generated by the healthcare worker. Also, the data recognition unit 120 may use results output by the machine learning model to update the machine learning model.

At least one of the data learning unit 110 and the data recognition unit 120 may be manufactured in the form of at least one hardware chip and installed in an electronic device. For example, at least one of the data learning unit 110 and the data recognition unit 120 may be manufactured in the form of a dedicated hardware chip for artificial intelligence (AI) or may be manufactured as a part of an existing general purpose processor (e.g., a CPU or an application processor) or a dedicated graphics processor (e.g., a graphics processing unit (GPU)) and installed in various electronic devices.

In addition, the data learning unit 110 and the data recognition unit 120 may be separately installed in different electronic devices. For example, one of the data learning unit 110 and the data recognition unit 120 may be included in an electronic device, and the other may be included in a server. Also, the data learning unit 110 and the data recognition unit 120 communicate with each other by wire or wirelessly so that information on the machine learning model built by the data learning unit 110 may be provided to the data recognition unit 120 and data input to the data recognition unit 120 may be provided to the data learning unit 110 as additional training data.

Meanwhile, at least one of the data learning unit 110 and the data recognition unit 120 may be implemented as a software module. When at least one of the data learning unit 110 and the data recognition unit 120 is implemented as a software module (or a program module including an instruction), the software module may be stored in a memory or a non-transitory computer-readable medium. In this case, at least one software module may be provided by an operating system (OS) or a certain application. Alternatively, some of the at least one software module may be provided by the OS, and other may be provided by a certain application.

The data learning unit 110 according to an embodiment of the present disclosure may include a data acquisition unit 111, a preprocessing unit 112, a training data selection unit 113, a model training unit 114, and a model evaluation unit 115.

The data acquisition unit 111 may acquire data required for machine learning. Since a lot of data is required for learning, the data acquisition unit 111 may receive a data set including a plurality of pieces of data.

Label information may be allocated to each of the plurality of pieces of data. The label information may be information describing each of the plurality of pieces of data. The label information may be information to be drawn by the target task. The label information may be acquired from a user input, a memory, or results of the machine learning model. For example, when the target task determines information related to the accuracy of report information generated by healthcare workers from medical images and the report information generated by the healthcare workers on the basis of the medical images, the plurality of pieces of data may be the plurality of medical images and the plurality of pieces of report information of the healthcare workers, and the label information may be the accuracy of the report information generated by the healthcare workers.

The preprocessing unit 112 may preprocess the acquired data so that the received data may be used in machine learning. The preprocessing unit 112 may process the acquired data set into a preset format so that the model training unit 114, which will be described below, may use the data.

The training data selection unit 113 may select data required for learning from among the pieces of preprocessed data. The selected data may be provided to the model training unit 114. The training data selection unit 113 may select data required for learning from among the pieces of preprocessed data according to a preset criterion. Also, the training data selection unit 113 may select data according to a criterion which is preset through learning caused by the model training unit 114 to be described below. The model training unit 114 may learn a criterion for label information to be output on the basis of the data set. Also, the model training unit 114 may perform machine learning using the data set and label information of the data set as training data. Further, the model training unit 114 may perform machine learning by additionally using a previously acquired machine learning model. In this case, the previously acquired machine learning model may be a model which has been built in advance. For example, the machine learning model may be a model which has been built in advance on the basis of input basic training data.

The machine teaming model may be built in consideration of the application field thereof, the purpose thereof, the computing performance of a device, or the like. The machine learning model may be based on a neural network. For example, a deep neural network (DNN), a recurrent neural network (RNN), a long short-term memory (LSTM) model, a bidirectional recurrent deep neural network (BRDNN), a convolutional neural network (CNN), etc. may be used as the machine learning model, but the machine learning model is not limited thereto.

According to various embodiments, when a plurality of machine learning models have been built in advance, the model training unit 114 may determine a machine learning model whose basic training data is in close relation to the input training data as a machine learning model to train. In this case, basic training data may have been classified according to data types, and machine learning models may have been built in advance according to the data types. For example, the basic training data may have been previously classified by various criteria, such as a location where training data has been generated, a time when training data has been generated, the size of training data, the generator of training data, and the type of an object in training data.

The model training unit 114 may train the machine learning model using learning algorithms including, for example, error backpropagation or gradient descent.

The model training unit 114 may train the machine learning model through supervised learning in which, for example, training data is used as input values. Also, the model training unit 114 may acquire the machine learning model through unsupervised learning in which, for example, the types of data required for a target task are learned without supervision to find a criterion for the target task. Further, the model training unit 114 may acquire the machine learning model through semi-supervised learning or active learning. Moreover, the model training unit 114 may train the machine learning model through reinforcement learning in which, for example, feedback about whether results of a target task obtained through learning are correct.

When the machine learning model is trained, the model training unit 114 may store the trained machine learning model. In this case, the model training unit 114 may store the trained machine learning model in the memory of an electronic device including the data recognition unit 120. Alternatively, the model training unit 114 may store the trained machine learning model in a memory of a server which is connected to an electronic device through a wire or wireless network.

The memory in which the trained machine learning model is stored may also store, for example, an instruction or data associated with at least one other element of an electronic device. Also, the memory may store software and/or a program. The program may include, for example, a kernel, middleware, an application programming interface (API), an application program (or "application"), and/or the like.

The model evaluation unit 115 may input evaluation data to the machine learning model and cause the model training unit 114 to train the machine learning model again when results output from the evaluation data do not satisfy a certain criterion. In this case, the evaluation data may be preset data for evaluating a machine learning model.

For example, when the number or ratio of pieces of evaluation data whose recognition results are not correct among the output results of the trained machine learning model from the evaluation data exceeds a preset threshold value, the model evaluation unit 115 may evaluate that the certain criterion is not satisfied. For example, the certain criterion may be defined to be a ratio of 2%. In this case, when the trained machine teaming model outputs wrong recognition results from more than 20 pieces of evaluation data among a total of 1,000 pieces of evaluation data, the model evaluation unit 115 may evaluate the trained machine learning model not to be appropriate.

Meanwhile, when there are a plurality of trained machine learning models, the model evaluation unit 115 may evaluate whether each trained machine learning model satisfies the certain criterion and determine a model satisfying the certain criterion as a final machine learning model. When a plurality of models satisfy the certain criterion, the model evaluation unit 115 may determine any one model or a certain number of models as final machine learning models in decreasing order of evaluation score.

Meanwhile, at least one of the data acquisition unit 111, the preprocessing unit 112, the training data selection unit 113, the model training unit 114, and the model evaluation unit 115 may be manufactured in the form of at least one hardware chip and installed in an electronic device. For example, at least one of the data acquisition unit 111, the preprocessing unit 112, the training data selection unit 113, the model training unit 114, and the model evaluation unit 115 may be manufactured in the form of a dedicated hardware chip for AI or may be manufactured as a part of an existing general purpose processor (e.g., a CPU or an application processor) or a dedicated graphics processor (e.g., a GPU) and installed in the aforementioned various electronic devices.

Also, the data acquisition unit 111, the preprocessing unit 112, the training data selection unit 113, the model training unit 114, and the model evaluation unit 115 may be installed in one electronic device or separately installed in different electronic devices. For example, some of the data acquisition unit 111, the preprocessing unit 112, the training data selection unit 113, the model training unit 114, and the model evaluation unit 115 may be included in an electronic device, and others may be included in a server.

Further, at least one of the data acquisition unit 111, the preprocessing unit 112, the training data selection unit 113, the model training unit 114, and the model evaluation unit 115 may be implemented as a software module. When at least one of the data acquisition unit 111, the preprocessing unit 112, the training data selection unit 113, the model training unit 114, and the model evaluation unit 115 is implemented as a software module (or a program module including an instruction), the software module may be stored in a non-transitory computer-readable medium. In this case, at least one software module may be provided by the OS or a certain application. Alternatively, some of the least one software module may be provided by the OS, and other may be provided by a certain application.

The data recognition unit 120 according to an embodiment of the present disclosure may include a data acquisition unit 121, a preprocessing unit 122, a recognition data selection unit 123, a recognition result providing unit 124, and a model update unit 125.

The data acquisition unit 121 may receive input data. The preprocessing unit 122 may preprocess the acquired input data so that the acquired input data may be used by the recognition data selection unit 123 or the recognition result providing unit 124.

The recognition data selection unit 123 may select required data from among the pieces of preprocessed data. The selected data may be provided to the recognition result providing unit 124. The recognition data selection unit 123 may select some or all of the pieces of preprocessed data according to a preset criterion. Also, the recognition data selection unit 123 may select data according to a criterion which is preset through learning caused by the model training unit 114.

The recognition result providing unit 124 may acquire result data by applying the selected data to a machine learning model. The machine learning model may be generated by the model training unit 114. The recognition result providing unit 124 may output result data.

The model update unit 125 may cause the machine teaming model to be updated on the basis of evaluation of recognition results provided by the recognition result providing unit 124. For example, the model update unit 125 may provide the recognition results provided by the recognition result providing unit 124 to the model training unit 114 so that the model training unit 114 may update the machine learning model.

Meanwhile, at least one of the data acquisition unit 121, the preprocessing unit 122, the recognition data selection unit 123, the recognition result providing unit 124, and the model update unit 125 in the data recognition unit 120 may be manufactured in the form of at least one hardware chip and installed in an electronic device. For example, at least one of the data acquisition unit 121, the preprocessing unit 122, the recognition data selection unit 123, the recognition result providing unit 124, and the model update unit 125 may be manufactured in the form of a dedicated hardware chip for AI or may be manufactured as a part of an existing general purpose processor (e.g., a CPU or an application processor) or a dedicated graphics processor (e.g., a GPU) and installed in the aforementioned various electronic devices.

Also, the data acquisition unit 121, the preprocessing unit 122, the recognition data selection unit 123, the recognition result providing unit 124, and the model update unit 125 may be installed in one electronic device or separately installed in different electronic devices. For example, some of the data acquisition unit 121, the preprocessing unit 122, the recognition data selection unit 123, the recognition result providing unit 124, and the model update unit 125 may be installed in an electronic device, and others may be installed in a server.

Further, at least one of the data acquisition unit 121, the preprocessing unit 122, the recognition data selection unit 123, the recognition result providing unit 124, and the model update unit 125 may be implemented as a software module. When at least one of the data acquisition unit 121, the preprocessing unit 122, the recognition data selection unit 123, the recognition result providing unit 124, and the model update unit 125 is implemented as a software module (or a program module including an instruction), the software module may be stored in a non-transitory computer-readable medium. In this case, at least one software module may be provided by the OS or a certain application. Alternatively, some of the least one software module may be provided by the OS, and other may be provided by a certain application.

A device and method for the data learning unit 110 to sequentially machine-learn data sets will be described in further detail below.

Figure 2:
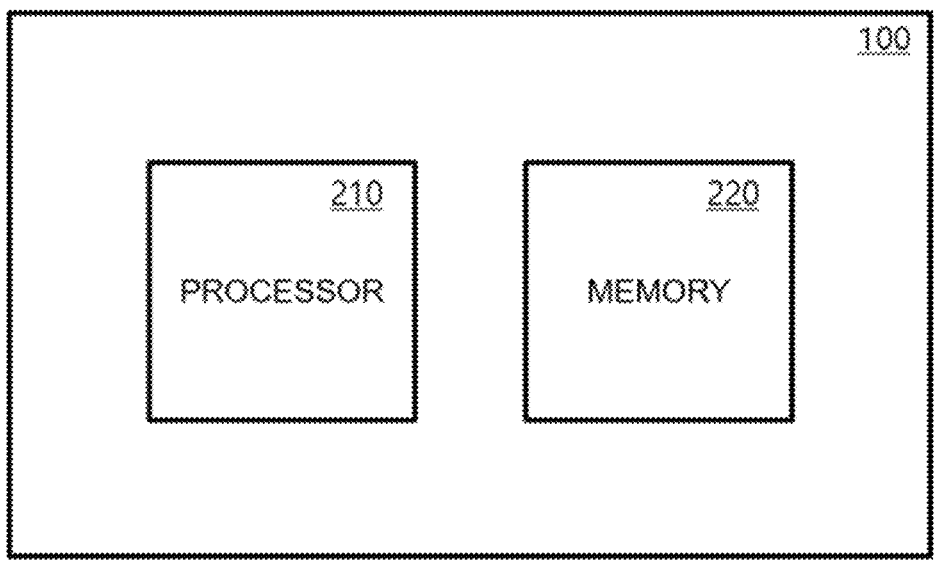
FIG. 2 is a block diagram of a medical image analysis device according to an embodiment of the present disclosure.

FIG. 2 is a block diagram of a medical image analysis device according to an embodiment of the present disclosure.

The medical image analysis device 100 may include a processor 210 and a memory 220. The processor 210 may perform instructions stored in the memory 220.

As described above, the medical image analysis device 100 may include at least one of the data learning unit 110 and the data recognition unit 120. At least one of the data learning unit 110 and the data recognition unit 120 may be implemented by the processor 210 and the memory 220.

Operation of the medical image analysis device 100 will be described in detail below.

Figure 3:
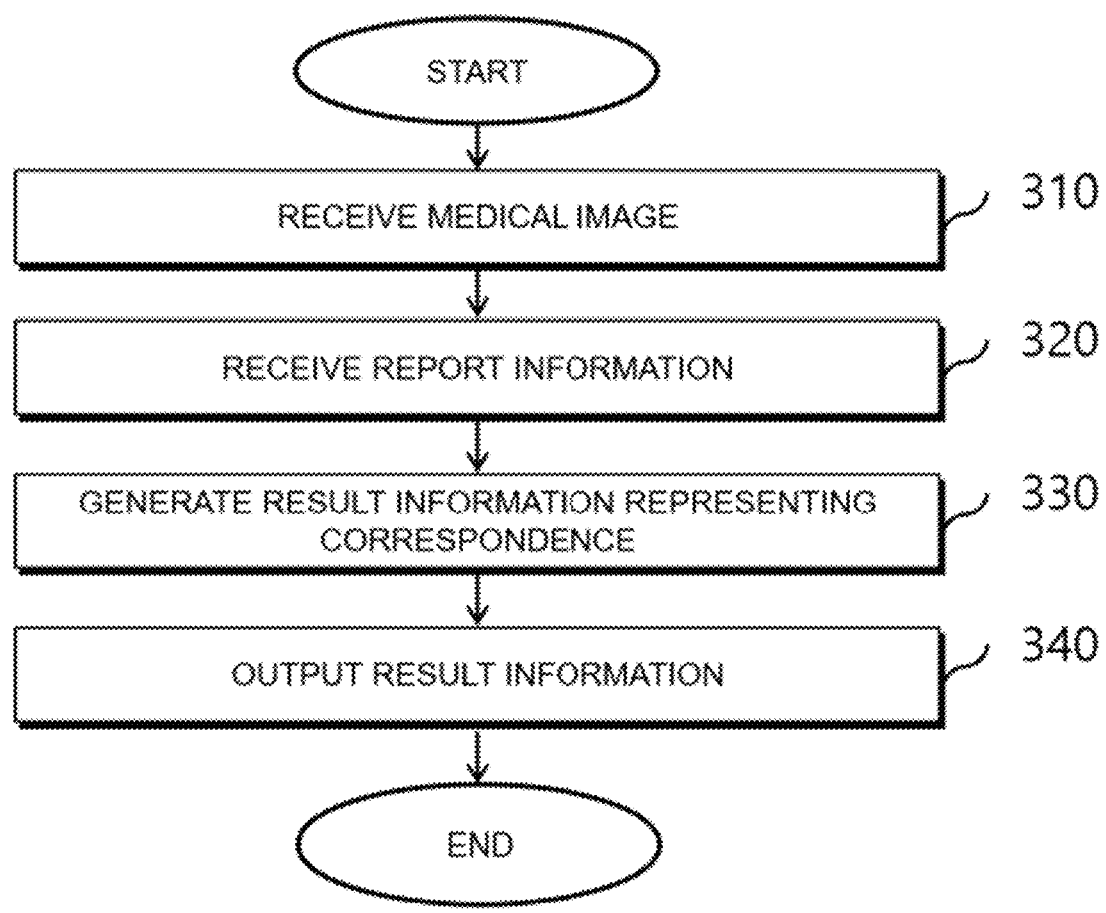
FIG. 3 is a flowchart illustrating an operation of a medical image analysis device according to an embodiment of the present disclosure.

FIG. 3 is a flowchart illustrating an operation of a medical image analysis device according to an embodiment of the present disclosure.

The medical image analysis device 100 may perform an operation 310 of receiving a medical image from a medical image apparatus. The medical image may be at least one of a computed tomography (CT) image, an X-ray image, a mammography image, and a magnetic resonance imaging (MRI) image. However, the medical image is not limited thereto and may include a moving image or an image represented as a graph. An image represented as a graph may include an elektrokardiogramm (EKG) graph.

The medical image analysis device 100 may receive a medical image from a medical image apparatus by wire or wirelessly. The medical image apparatus may include a medical imaging device and a picture archiving and communication system. Also, the medical image analysis device 100 may acquire a medical image stored in the memory 220.

The medical image analysis device 100 may perform an operation 320 of receiving report information which is a healthcare worker's judgement result of the medical image. The medical image analysis device 100 may receive the report information by wire or wirelessly. The medical image analysis device 100 may receive the report information from an input unit (not shown).

The medical image analysis device 100 may receive medical images and report information in real time. In other words, the medical image analysis device 100 may receive as soon as a medical image or report information is generated. Also, since a medical image apparatus, a gateway, or a server may collect and transmit a plurality of pieces of report information or a plurality of medical images to the medical image analysis device 100 in non-real-time, the medical image analysis device 100 may receive the plurality of pieces of report information or the plurality of medical images in non-real-time. Also, the medical image analysis device 100 may receive a medical image and report information automatically or manually.

Report information may be analysis results made by a healthcare worker who has analyzed a medical image. The report information may include window information of the medical image. The window information may include window center information and window width information. The window center information and the window width information may be information for adjusting brightness and contrast of the medical image. In addition, the report information may include various kinds of numerical information related to the medical image. Also, the report information may include at least one of information on a lesion and information on a patient. Further, the report information may include information on a marker shown on the image. The marker information may include at least one pixel value or location information of the marker. The marker information may represent the location or length of a region of interest marked by the healthcare worker.

The information on a lesion may include at least one of the name, type, size, location, and seriousness of a lesion shown in the medical image. Also, the information on the patient may include at least one of the case history, age, sex, and family history of the patient.

The medical image analysis device 100 may perform an operation 330 of generating result information representing correspondence between first lesion information based on the medical image and second lesion information based on the report information by applying the first lesion information and the second lesion information to a third analysis model. The first lesion information and the second lesion information may be information related to a lesion in the medical image. The medical image analysis device 100 may generate result information representing correspondence between the first lesion information acquired on the basis of the medical image and the second lesion information acquired on the basis of the report information by applying the first lesion information and the second lesion information to the third analysis model. The first lesion information, the second lesion information, and the third analysis model will be described in further detail below with reference to FIGS. 4 to 9.

The result information may represent correspondence or similarity between the first lesion information and the second lesion information. According to an embodiment of the present disclosure, the medical image analysis device 100 may digitally represent the correspondence between the first lesion information and the second lesion information. For example, the medical image analysis device 100 may represent the result information as 1 when the first lesion information is identical to the second lesion information, and may represent the result information as 0 when the first lesion information is not identical to the second lesion information. However, the result information is not limited thereto, and the medical image analysis device 100 may represent the result information as 0 when the first lesion information is identical to the second lesion information, and may represent the result information as 1 when the first lesion information is not identical to the second lesion information.

According to another embodiment of the present disclosure, the medical image analysis device 100 may represent the similarity between the first lesion information and the second lesion information by a real number or a natural number. For example, the medical image analysis device 100 may represent the similarity by a larger number when the first lesion information is more similar to the second lesion information, and may represent the similarity by a smaller number when the first lesion information is less similar to the second lesion information. However, the similarity is not limited thereto, and the medical image analysis device 100 may represent the similarity by a smaller number when the first lesion information is more similar to the second lesion information, and may represent the similarity by a larger number when the first lesion information is less similar to the second lesion information.

The medical image analysis device 100 may determine result information representing whether the first lesion information is identical to the second lesion information by comparing the similarity with a threshold value. For example, when the similarity is greater than the threshold value, the medical image analysis device 100 may make the result information represent that the first lesion information is identical to the second lesion information. Also, when the similarity is less than the threshold value, the medical image analysis device 100 may make the result information represent that the first lesion information is not identical to the second lesion information. However, the result information is not limited thereto, and the medical image analysis device 100 may make the result information represent that the first lesion information is not identical to the second lesion information when the similarity is greater than the threshold value, and may make the result information represent that the first lesion information is identical to the second lesion information when the similarity is less than the threshold value.

The medical image analysis device 100 may perform an operation 340 of outputting the result information. The result information may be transmitted by wire or wirelessly to a hospital server, a terminal of the healthcare worker, a terminal of the patient, or a payer server. The result information may be displayed on a display of the medical image analysis device 100 or output through a speaker.

When the report information of the healthcare worker represents that there is no lesion in the medical image, the medical image analysis device 100 may acquire the result information about the medical image on the basis of the operations of FIG. 3. On the other hand, the medical image analysis device 100 may determine that a lesion exists in the medical image on the basis of the result information. In other words, the report information 421 of the healthcare worker may be determined to be wrong. For example, the report information of the healthcare worker may represent that the medical image is normal. However, the medical image analysis device 100 may determine that there is microcalcification in the medical image. The medical image analysis device 100 may display a lesion that the healthcare worker has not been able to detect but the medical image analysis device 100 has detected. Therefore, the medical image analysis device 100 may examine the medical image which has been interpreted by the healthcare worker in a duplicate manner and prevent a lesion from being ignored.

Also, when the report information of the healthcare worker represents that there is a lesion in the medical image, the medical image analysis device 100 may acquire the result information about the medical image on the basis of the operations of FIG. 3. On the other hand, the medical image analysis device 100 may determine that a lesion exists in the medical image but there is an ignored lesion in the report information or a lesion described in the report information is wrong on the basis of the result information. For example, the report information of the healthcare worker may represent that only a pneumothorax has been detected in a chest X-ray image, but the medical image analysis device 100 may detect a pneumothorax and a lung nodule on the basis of a machine learning model.

The medical image analysis device 100 may output the result information so that the healthcare worker may take necessary measures. For example, the healthcare worker may review the medical image on the basis of the result information. Alternatively, the medical image analysis device 100 may change work lists of healthcare workers so that a healthcare worker other than the healthcare worker who has interpreted the medical image may examine the medical image. Otherwise, the medical image analysis device 100 may change work lists of healthcare workers so that a plurality of healthcare workers may examine the medical image. In addition, the healthcare worker may suggest that the patient gets an additional checkup. Therefore, the medical image analysis device 100 may improve analysis results of the medical image.

Figure 4:
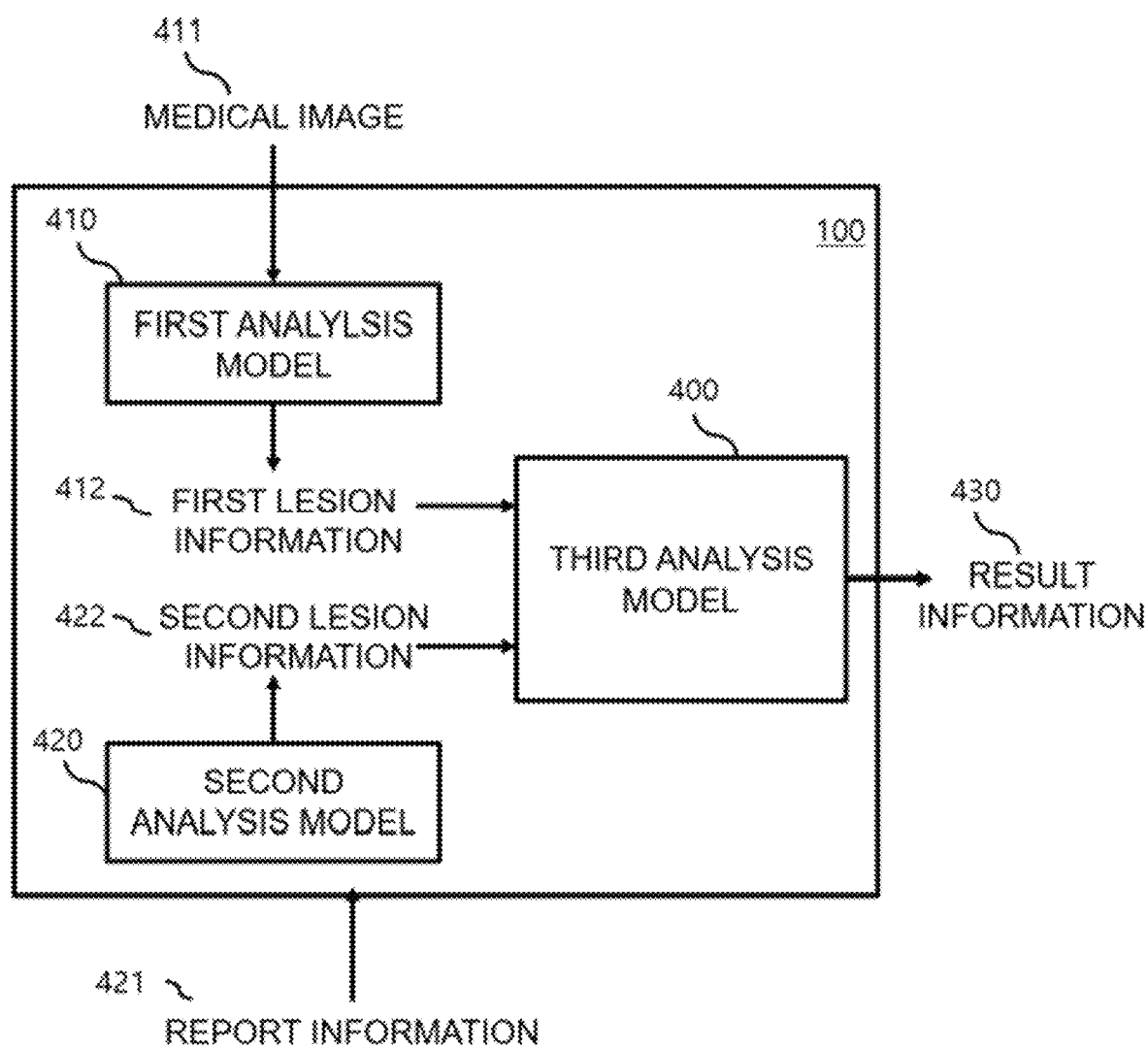
FIG. 4 is a block diagram of a medical image analysis device according to an embodiment of the present disclosure.

FIG. 4 is a block diagram of a medical image analysis device according to an embodiment of the present disclosure.

The medical image analysis device 100 may include a first analysis model, a second analysis model, or a third analysis model. The first analysis model or the second analysis model may be omitted.

The medical image analysis device 100 may receive a medical image 411. The medical image analysis device 100 may perform an operation of acquiring first lesion information by applying the medical image 411 to a first analysis model 410. The first analysis model 410 may be a model which has machine-learned correlations between a plurality of past medical images and a plurality of pieces of first past lesion information corresponding to the plurality of past medical images.

The term "past" may denote training data for machine learning. For example, the plurality of past medical images and the plurality of pieces of first past lesion information may denote training data used for machine-learning of the first analysis model 410.

The medical image analysis device 100 may not include the first analysis model 410. In this case, first lesion information 412 may include the medical image 411.

Also, the medical image analysis device 100 may perform an operation of acquiring second lesion information 422 by applying report information 421 to a second analysis model 420. The second analysis model 420 may include a model which has machine-learned correlations between a plurality of pieces of past report information and a plurality of pieces of second past lesion information corresponding to the plurality of pieces of past report information. The term "past" may denote training data for machine learning. For example, the plurality of pieces of past report information and the plurality of pieces of second past lesion information may denote training data used for machine-learning of the second analysis model 420.

The second analysis model 420 may not be a machine learning model but may be a rule-based model which extracts information from report information. For example, the second analysis model 420 may be a model for determining whether lesion information is included in report information. Here, the lesion information may include various kinds of information related to a lesion. For example, the lesion information may include at least one of the name, type, location, and size of a lesion.

The medical image analysis device 100 may not include the second analysis model 420. In this case, the second lesion information 422 may include the report information 421.

The medical image analysis device 100 may perform an operation of acquiring result information 430 by applying the first lesion information 412 and the second lesion information 422 to a third analysis model 400. The third analysis model 400 may be a model which has machine-learned a plurality of pieces of first past lesion information, a plurality of pieces of second past lesion information, and past result information representing past similarity between the plurality of pieces of first past lesion information and the plurality of pieces of second past lesion information. The term "past" may denote training data for machine learning. For example, the plurality of pieces of first past lesion information, the plurality of pieces of second past lesion information, and the past result information may denote training data used for machine-learning of the third analysis model 400.

The first lesion information 412 may include at least one of a medical image 411, first lesion presence information representing whether there is a lesion in the medical image 411, first lesion type information, first lesion area information including a location of a lesion in the medical image 411 and a size of the lesion, and first report information automatically generated from the medical image 411 by the first analysis model 410.

As described above, the medical image analysis device 100 may not include the first analysis model 410. When the medical image analysis device 100 does not include the first analysis model 410, the first lesion information 412 may be the medical image 411. The third analysis model 400 may receive the medical image 411.

The medical image analysis device 100 may generate the first lesion presence information which is one-dimensional information by applying the medical image 411 to the first analysis model 410. The first analysis model 410 may be a model which has machine-learned relations between past medical images and past label information representing whether a lesion exists in the past medical images.

According to an embodiment, the first lesion presence information may have a value of 0 or 1. For example, when the first analysis model 410 has detected a lesion in the medical image 411, the first lesion presence information may be 1. Also, when the first analysis model 410 has not detected a lesion in the medical image 411, the first lesion presence information may be 0. However, the first lesion presence information is not limited thereto. When the first analysis model 410 has detected a lesion in the medical image 411, the first lesion presence information may be 0, and when the first analysis model 410 has not detected a lesion in the medical image 411, the first lesion presence information may be 1. The third analysis model 400 may receive the first lesion presence information.

Also, the medical image analysis device 100 may acquire the first lesion type information by applying the medical image 411 to the first analysis model 410. The first analysis model 410 may be a model which has machine-learned relations between past medical images and type information of a past lesion existing in the past medical images.

The first lesion type information may include a code representing a lesion or a name of the lesion. When the first analysis model 410 has not detected a lesion in the medical image 411, the first lesion type information may have a value of 0 or null.

The first lesion information 412 may include the first lesion area information. The medical image analysis device 100 may acquire the first lesion area information by applying the medical image 411 to the first analysis model 410. The first analysis model 410 may be a model which has machine-learned relations between past medical images and location information of a past lesion corresponding to the past medical images.

According to an embodiment of the present disclosure, the first lesion area information may be two-dimensional information. The first lesion area information may be shown by a marker on the medical image 411. The marker represents a location and size of a lesion in the medical image 411 and may be displayed by using at least one pixel included in the medical image 411. The marker may be in a circular, oval, quadrangular, or triangular shape.

According to an embodiment of the present disclosure, the first lesion area information may represent a location and size of a lesion. For example, the first lesion area information may include coordinate values representing the location of the lesion. Also, the first lesion area information may include a value representing the size of the lesion. The size may include at least one of the radius, diameter, area, volume, and the length of one side. The third analysis model 400 may receive the first lesion area information.

The first lesion information 412 may include first report information which has been automatically generated from the medical image 411 by the first analysis model 410. The first analysis model 410 may be a model which has machine-learned relations between past medical images and past report information related to a lesion included in the past medical images.

The medical image analysis device 100 may generate first report information about the medical image 411 by applying the medical image 411 to the first analysis model 410. A healthcare worker may modify the first report information automatically generated by the medical image analysis device 100 without writing a new report. Also, a healthcare worker may determine the modified report information as final diagnosis results and input the final diagnosis results to the medical image analysis device 100. The final diagnosis results may be the report information 421. Also, the third analysis model 400 may receive the first report information.

The second lesion information 422 may include at least one of report information, second lesion presence information representing whether there is a lesion on the basis of the report information, second lesion type information, and second lesion area information including a location or size of a lesion acquired on the basis of the report information.

As described above, the medical image analysis device 100 may not include the second analysis model 420. When the medical image analysis device 100 does not include the second analysis model 420, the second lesion information 422 may be the report information 421. The third analysis model 400 may receive the report information 421.

The medical image analysis device 100 may generate the second lesion presence information which is one-dimensional information by applying the report information 421 to the second analysis model 420. The second analysis model 420 may be a model which has machine-learned relations between past report information and label information representing whether information related to a lesion exists in the past report information.

According to an embodiment, the second lesion presence information may have a value of 0 or 1. For example, when the second analysis model 420 has detected information representing that there is a lesion in the medical image 411 in the report information 421, the second lesion presence information may be 1. Also, when the second analysis model 420 has not detected information representing that there is a lesion in the medical image 411 in the report information 421, the second lesion presence information may be 0. However, the second lesion presence information is not limited thereto. When the second analysis model 420 has detected information representing that there is a lesion in the medical image 411 in the report information 421, the second lesion presence information may be 0, and when the second analysis model 420 has not detected information representing that there is a lesion in the medical image 411 in the report information 421, the second lesion presence information may be 1. The third analysis model 400 may receive the second lesion presence information.

Also, the medical image analysis device 100 may acquire the second lesion type information by applying the report information 421 to the second analysis model 420. The second analysis model 420 may be a model which has machine-learned relations between past report information and type information of a past lesion existing in the past report information.

The second lesion type information may include a code representing a lesion or a name of the lesion. When the second analysis model 420 has not detected a lesion in the report information 421, the second lesion type information may have a value of 0 or null.

The second lesion information 422 may include the second lesion area information. The medical image analysis device 100 may acquire the second lesion area information by applying the report information 421 to the second analysis model 420. The second analysis model 420 may be a model which has machine-learned relations between past report information and location information of a lesion described in the past report information.

According to an embodiment of the present disclosure, the second lesion area information may be two-dimensional information. The second lesion area information may be shown by a marker on the medical image 411 or a template image. The marker represents a location and size of a lesion in the medical image 411 and may be displayed by using at least one pixel included in the medical image 411 or the template image. The marker may be in various shapes, such as a circle, oval, quadrangle, or triangle. The template image is an image corresponding to the body part of a patient shown in the medical image 411 and may be stored in the memory of the medical image analysis device 100.

According to an embodiment of the present disclosure, the second lesion area information may represent a location and size of a lesion. For example, the second lesion area information may include coordinate values representing the location of the lesion. Also, the second lesion area information may include a value representing the size of the lesion. The size may include at least one of the radius, diameter, area, volume, and the length of one side. The third analysis model 400 may receive the second lesion area information.

Figure 5:
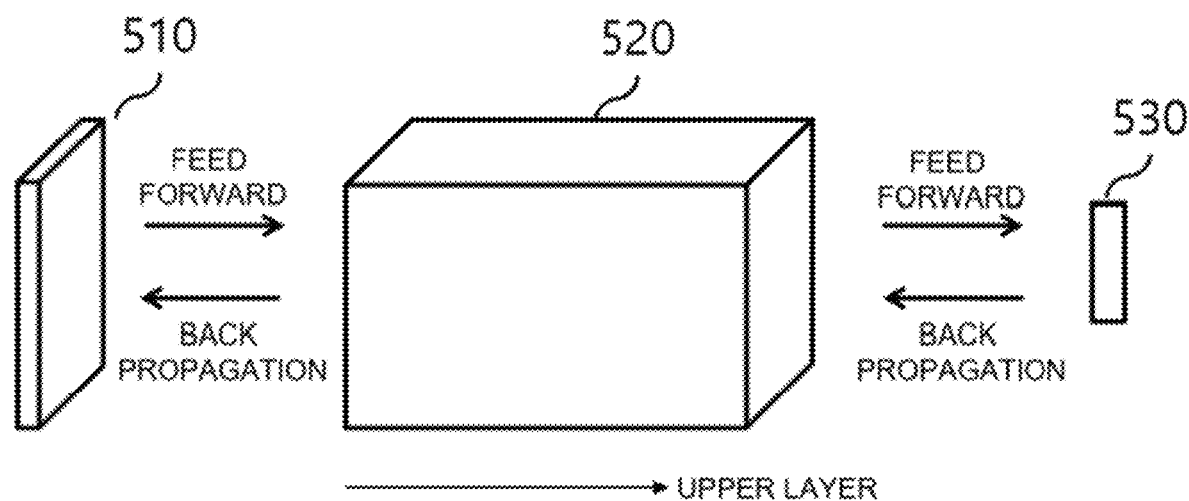
FIG. 5 is a diagram illustrating a process of generating a machine learning model according to an embodiment of the present disclosure.

FIG. 5 is a diagram illustrating a process of generating a machine learning model according to an embodiment of the present disclosure.

As described above, the first analysis model 410 and the second analysis model 420 may be machine teaming models.

According to an embodiment of the present disclosure, the medical image analysis device 100 may generate first lesion presence information by applying the medical image 411 to the first analysis model 410. The first analysis model 410 may be a model which has machine-learned relations between a plurality of past medical images and a plurality of pieces of past lesion presence information each corresponding to the plurality of past medical images.

FIG. 5 is a block diagram showing a process in which the medical image analysis device 100 generates a machine teaming model on the basis of a plurality of pieces of data. The medical image analysis device 100 may receive input data 510 and output data 530 to acquire the first analysis model 410. The input data 510 may be a plurality of past medical images. Also, the output data 530 may be a plurality of pieces of past lesion presence information. The medical image analysis device 100 may update a hidden layer 520 through feed forwards and back propagations for machine learning of a model which generates the output data 530 from the input data 510. The medical image analysis device 100 may generate the first analysis model 410 by updating the hidden layer 520 on the basis of the plurality of past medical images and the plurality of pieces of past lesion presence information.

The medical image analysis device 100 may generate first lesion presence information by applying the medical image 411 to the generated first analysis model 410. In other words, the medical image 411 is used as the input data 510 for a feed forward, and the output data 530 may be generated by the feed forward through the hidden layer 520. The output data 530 may be first lesion presence information. The medical image analysis device 100 may determine first feature information, which is included in the hidden layer 520 immediately before the output data 530, as first lesion information. In other words, the first lesion information may include first feature information related to the hidden layer 520 of the first analysis model for generating first lesion presence information from a medical image. For example, the first feature information may include values included in an uppermost layer of the hidden layer 520 when the medical image is fed forward.

Likewise, an embodiment included in the second lesion information is described as follows. The medical image analysis device 100 may receive input data 510 and output data 530 to acquire the second analysis model 420. The input data 510 may be a plurality of pieces of past report information. Also, the output data 530 may be a plurality of pieces of past lesion presence information described in the plurality of pieces of past report information. The medical image analysis device 100 may update a hidden layer 520 through feed forwards and back propagations for machine learning of a model which generates the output data 530 from the input data 510. The medical image analysis device 100 may generate the second analysis model 420 by updating the hidden layer 520 on the basis of the plurality of pieces of past report information and the plurality of pieces of past lesion presence information.

The medical image analysis device 100 may generate second lesion presence information by applying the report information 421 to the generated second analysis model 420. In other words, the report information 421 is used as the input data 510 for a feed forward, and the output data 530 may be generated by the feed forward through the hidden layer 520. The medical image analysis device 100 may determine second feature information, which is included in the hidden layer 520 immediately before the output data 530, as second lesion information. In other words, the second lesion information may include second feature information about at least one feature related to the hidden layer 520 of the second analysis model for generating second lesion presence information from report information. For example, the second feature information may include values included in the uppermost layer of the hidden layer 520 when the report information is fed forward.

The medical image analysis device 100 may generate the third analysis model 400 which has machine-learned relations among the first feature information, the second feature information, and label information representing similarity between the first feature information and the second feature information. The medical image analysis device 100 may acquire similarity between lesion information included in a medical image and lesion information described in report information using the generated first analysis model 410, second analysis model 420, and third analysis model 400.

Also, the medical image analysis device 100 may receive the input data 510 and the output data 530 to acquire the third analysis model 400. The input data 510 may be a plurality of pieces of first past lesion information and a plurality of pieces of second past lesion information. Also, the output data 530 may be a plurality of pieces of past result information representing correspondence between the plurality of pieces of first past lesion information and the plurality of pieces of second past lesion information. The medical image analysis device 100 may update the hidden layer 520 through feed forwards and back propagations for machine learning of a model which generates the output data 530 from the input data 510. The medical image analysis device 100 may generate the third analysis model 400 by updating the hidden layer 520 on the basis of the plurality of pieces of first past lesion information, the plurality of pieces of second past lesion information, and the plurality of pieces of past result information.

Figure 6:
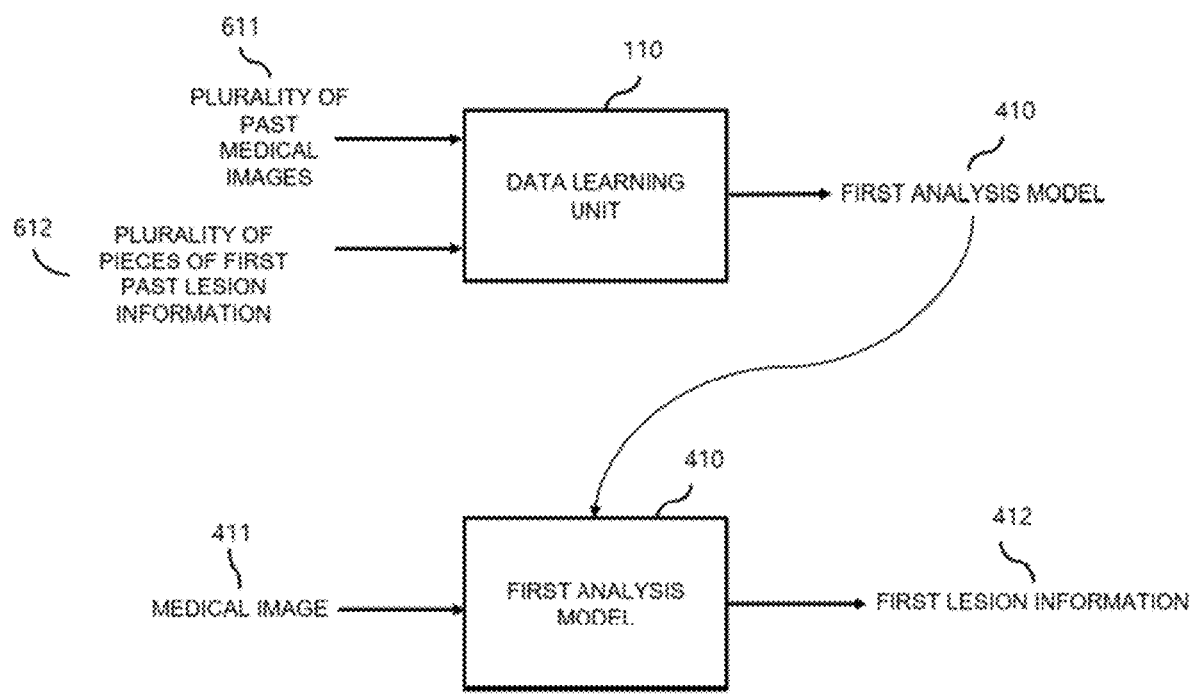
FIG. 6 is a diagram illustrating a first analysis model according to an embodiment of the present disclosure.

FIG. 6 is a diagram illustrating a first analysis model according to an embodiment of the present disclosure.

The first analysis model 410 may be a model which has machine-learned correlations between a plurality of past medical images 611 and a plurality of pieces of first past lesion information 612 corresponding to the plurality of past medical images 611. The plurality of past medical images 611 and the plurality of pieces of first past lesion information 612 corresponding to the plurality of past medical images 611 may be ground truth information. The ground truth information may be information determined to be correct by an expert.

The plurality of past medical images 611 and the plurality of pieces of first past lesion information 612 corresponding to the plurality of past medical images 611 may be acquired from an external server. For example, the external server may include at least one of a hospital server, a health insurance server, or a server of a governmental institution.

The plurality of pieces of first past lesion information 612 may be diagnosis results of the plurality of past medical images 611 made by healthcare workers. However, the plurality of pieces of first past lesion information 612 are not limited thereto and may be information generated on the basis of the plurality of past medical images 611 by a machine learning model. The plurality of pieces of first past lesion information 612 may include at least one of information on whether a lesion exists in the plurality of past medical images 611, lesion type information, location or size information of a lesion, and past report information generated on the basis of the plurality of past medical images 611 by healthcare workers.

The medical image analysis device 100 may generate the first analysis model 410 using the data learning unit 110 of FIG. 1 together with the plurality of past medical images 611 and the plurality of pieces of first past lesion information 612.

The medical image analysis device 100 may store the first analysis model 410 in the memory or transmit the first analysis model 410 to another medical image analysis device by wire or wirelessly.

The medical image analysis device 100 may receive the medical image 411. The medical image analysis device 100 may draw first lesion information 412 by applying the first analysis model 410 to the medical image 411. The medical image analysis device 100 may automatically acquire the first lesion information 412 on the basis of the first analysis model 410 without help of a healthcare worker.

The first lesion information 412 may include at least one of a medical image, first lesion presence information representing whether there is a lesion in the medical image, first lesion area information representing a location of a lesion in the medical image and a size of the lesion, and first report information automatically generated from the medical image by the first analysis model 410. Also, the first lesion information 412 may include first feature information related to a hidden layer of the first analysis model 410 for generating first lesion presence information from a medical image. The first feature information has been described above, and accordingly detailed description thereof will be omitted.

The medical image analysis device 100 may provide the first lesion information 412 to a healthcare worker. The healthcare worker may generate final diagnosis information by referring to the first lesion information 412.

Figure 7:
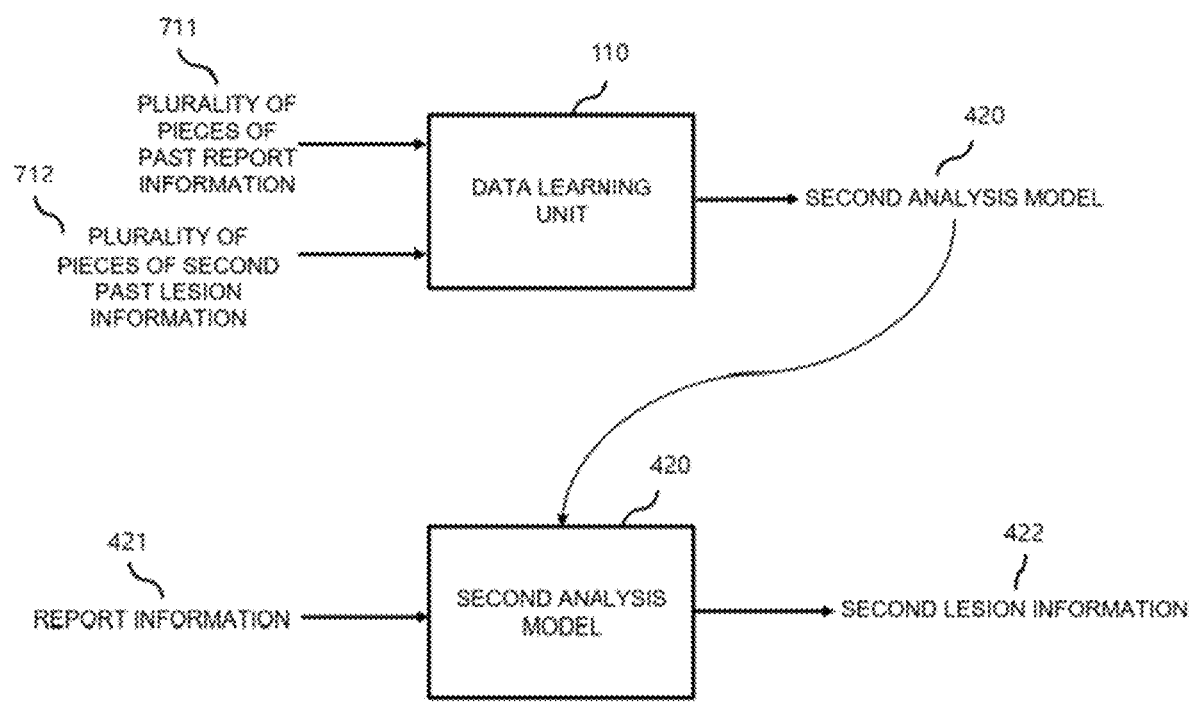
FIG. 7 is a diagram illustrating a second analysis model according to an embodiment of the present disclosure.

FIG. 7 is a diagram illustrating a second analysis model according to an embodiment of the present disclosure.

The second analysis model 420 may be a model which has machine-learned correlations between a plurality of pieces of past report information 711 and a plurality of pieces of second past lesion information 712 corresponding to the plurality of pieces of past report information 711. The plurality of pieces of past report information 711 and the plurality of pieces of second past lesion information 712 may be ground truth information.

The plurality of pieces of past report information 711 may be information received from a healthcare worker. The healthcare worker may analyze a medical image and write and store at least one piece of past report information in an external server. The at least one piece of past report information may include at least one of digital text information and image information. Also, the at least one piece of past report information may include diagnosis results written in handwriting by a person, a note made on the medical image by the healthcare worker, or the like.

The external server may cumulatively store at least one piece of past report information. The plurality of pieces of past report information 711 may be acquired from the external server. For example, the external server may include at least one of a hospital server, a health insurance server, and a server of a governmental institution.

The plurality of pieces of second past lesion information 712 corresponding to the plurality of pieces of past report information 711 may be label information about the past report information 711. The plurality of pieces of second past lesion information 712 may be information made by a person or information automatically extracted from the report information 711 on the basis of a machine learning model. The plurality of pieces of second past lesion information 712 may include at least one of information representing whether information related to a lesion exists in the past report information 711, lesion type information derived from past reports, and information representing a location or size of a lesion derived from the past report information 711.

The medical image analysis device 100 may generate the second analysis model 420 using the data learning unit 110 of FIG. together with the plurality of pieces of past report information 711 and the plurality of pieces of second past lesion information 712.

The medical image analysis device 100 may store the second analysis model 420 in the memory or transmit the second analysis model 420 to another medical image analysis device by wire or wirelessly.

The medical image analysis device 100 may receive report information 421. The medical image analysis device 100 may draw second lesion information 422 by applying the second analysis model 420 to the report information 421. The medical image analysis device 100 may automatically acquire the second lesion information 422, which is computer readable, from the report information 421 on the basis of the second analysis model 420.

The second lesion information 422 may include at least one of report information, second lesion presence information representing whether a lesion exists on the basis of the report information, and second lesion area information representing a location or size of a lesion on the basis of the report information. The second lesion information 422 may include second feature information related to a hidden layer of the second analysis model 420 for generating second lesion presence information from report information. The second feature information has been described above, and accordingly detailed description thereof will be omitted.

Through the processes described in FIGS. 6 and 7, the medical image analysis device 100 may acquire the first lesion information 412 and the second lesion information 422. The medical image analysis device 100 may generate result information representing whether the first lesion information 412 is identical to the second lesion information 422 on the basis of the third analysis model 400.

Figure 8:
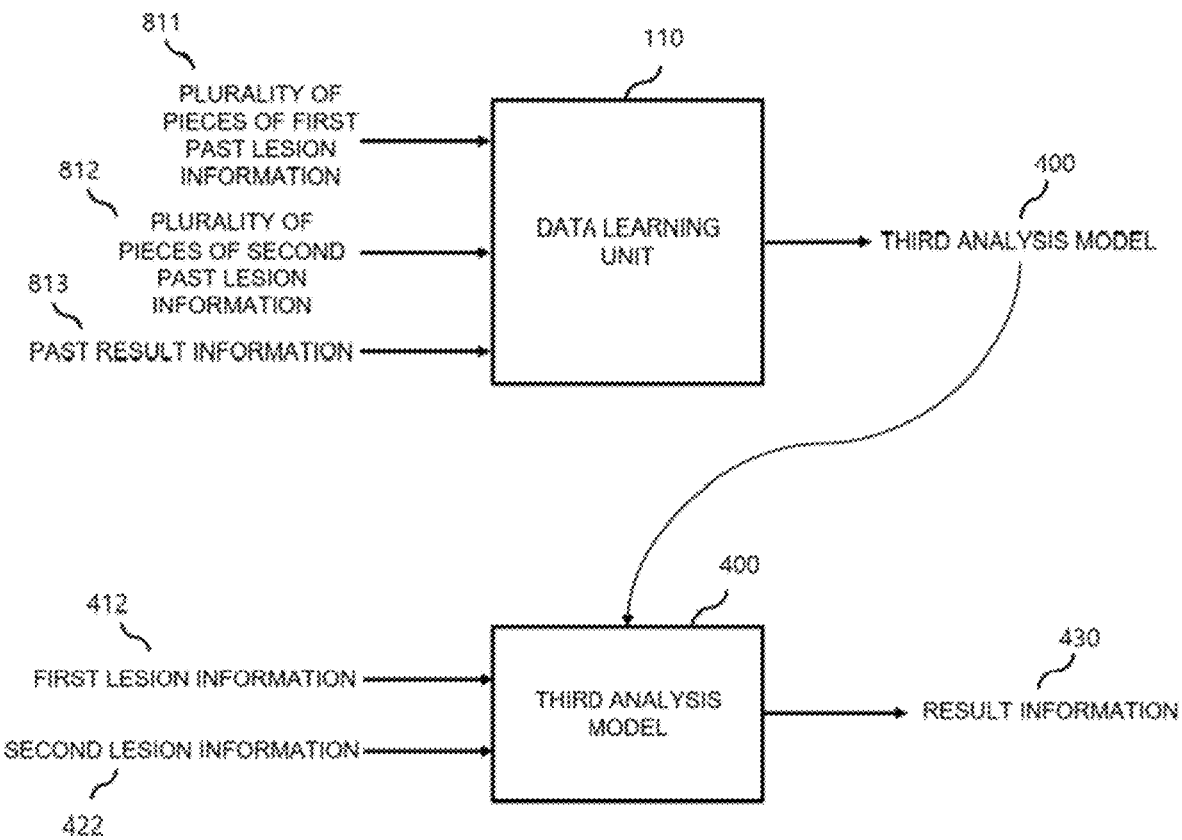
FIG. 8 is a diagram illustrating a third analysis model according to an embodiment of the present disclosure.

FIG. 8 is a diagram illustrating a third analysis model according to an embodiment of the present disclosure.

The third analysis model 400 may be a model which has machine-learned correlations among a plurality of pieces of first past lesion information 811, a plurality of pieces of second past lesion information 812, and past result information 813 representing correspondence between the plurality of pieces of first past lesion information 811 and the plurality of pieces of second past lesion information 812. The plurality of pieces of first past lesion information 811, the plurality of pieces of second past lesion information 812, and the past result information 813 may be ground truth information.

The plurality of pieces of first past lesion information 811 may be diagnosis results of the plurality of past medical images 611 made by healthcare workers. However, the plurality of pieces of first past lesion information 811 are not limited thereto and may be information generated on the basis of the past medical images 611 by a machine learning model. For example, the plurality of pieces of first past lesion information 811 may be information generated by the first analysis model 410 of FIG. 6. The first past lesion information 811 may include at least one of information on whether a lesion exists in the past medical images 611, lesion type information, location or size information of a lesion, and past report information generated on the basis of the past medical images 611 by healthcare workers.

Also, the first past lesion information 811 may include first past feature information related to a hidden layer of the first analysis model 410. As described above, the first analysis model 410 may be a model for acquiring first past lesion presence information from a past medical image. The first past feature information may include values included in the hidden layer of the first analysis model 410 when a past medical image is applied to the first analysis model 410. The first past feature information is similar to the first feature information which has been already described, and the same description will not be reiterated.

The plurality of pieces of second past lesion information 812 may be label information about past report information. The plurality of pieces of second past lesion information 812 may be information made by a person or information automatically extracted from report information on the basis of a machine learning model. For example, the plurality of pieces of second past lesion information 812 may be information generated by the second analysis model 420 of FIG. 7. The plurality of pieces of second past lesion information 812 may include at least one of information representing whether information related to a lesion exists in the past report information, lesion type information derived from past reports, and information representing a location or size of a lesion derived from the past report information.

Also, the second past lesion information 812 may include second past feature information related to a hidden layer of the second analysis model 420. As described above, the second analysis model 420 may be a model for acquiring second past lesion presence information from past report information. The second past feature information may include values included in the hidden layer of the second analysis model 420 when past report information is applied to the second analysis model 420. The second past feature information is similar to the second feature information which has been already described, and the same description will not be reiterated.

The past result information 813 representing the correspondence between the plurality of pieces of first past lesion information and the plurality of pieces of second past lesion information may be information representing correspondence or similarity between one of a plurality of pieces of first past lesion information 811 and a plurality of pieces of second past lesion information 812 corresponding thereto.

The past result information 813 may represent correspondence or similarity between the first past lesion information and the second past lesion information. The past result information 813 may be generated by a user's input or automatically generated by a machine learning model. According to an embodiment of the present disclosure, the medical image analysis device 100 may digitally represent the past result information 813 representing the correspondence between the first past lesion information and the second past lesion information. For example, the medical image analysis device 100 may represent the past result information 813 as 1 when the first past lesion information is identical to the second past lesion information, and may represent the past result information 813 as 0 when the first past lesion information is not identical to the second past lesion information. However, the past result information 813 is not limited thereto, and the medical image analysis device 100 may represent the past result information 813 as 0 when the first past lesion information is identical to the second past lesion information, and may represent the past result information 813 as 1 when the first past lesion information is not identical to the second past lesion information.

According to another embodiment of the present disclosure, the medical image analysis device 100 may represent the past result information 813, which represents the similarity between the first past lesion information and the second past lesion information, by a real number or a natural number. For example, the medical image analysis device 100 may represent the similarity by a larger number when the first past lesion information is more similar to the second past lesion information, and may represent the similarity by a smaller number when the first past lesion information is less similar to the second past lesion information. However, the past result information 813 is not limited thereto, and the medical image analysis device 100 may represent the past result information 813 by a smaller number when the first past lesion information is more similar to the second past lesion information, and may represent the past result information 813 by a larger number when the first past lesion information is less similar to the second past lesion information.

The medical image analysis device 100 may generate the third analysis model 400 by machine-learning the plurality of pieces of first past lesion information 811, the plurality of pieces of second past lesion information 812, and the past result information 813 representing the correspondence between the plurality of pieces of first past lesion information 811 and the plurality of pieces of second past lesion information 812.

However, the third analysis model 400 is not limited thereto and may not be a machine teaming model. In other words, the third analysis model 400 may be a rule-based model. The third analysis model 400 may be a model which simply determines whether the first lesion information 412 is identical to the second lesion information 422.

The third analysis model 400 employing a machine learning model may determine whether the first lesion information 412 is substantially identical to the second lesion information 422 even when the first lesion information 412 and the second lesion information 422 are in different formats. In the present disclosure, when the first lesion information 412 and the second lesion information 422 are in different formats, the third analysis model 400 should be construed as employing a machine learning model. Also, when the third analysis model 400 does not employ a machine learning model, it is possible to simply implement the third analysis model 400, and the processing rate may be relatively high.

The medical image analysis device 100 may store the third analysis model 400 in the memory or transmit the third analysis model 400 to another medical image analysis device by wire or wirelessly.

The medical image analysis device 100 may perform an operation of acquiring the result information 430 by applying the first lesion information 412 and the second lesion information 422 to the third analysis model 400. The first lesion information 412 and the second lesion information 422, which are inputs to the third analysis model 400, and the result information 430, which is an output from the third analysis model 400, have been described in FIG. 4, and the same description will not be reiterated.

The result information 430 which is an output from the third analysis model 400 will be described in further detail below.

According to an embodiment of the present disclosure, the medical image analysis device 100 may perform an operation of determining result information on the basis of whether first lesion presence information included in the first lesion information 412 is identical to second lesion presence information included in the second lesion information 422. In this case, the third analysis model 400 may not be a model generated by machine learning.

For example, the first lesion presence information included in the first lesion information 412 may have a value of 0 or 1. Also, the second lesion presence information included in the second lesion information 422 may have a value of 0 or 1.

The medical image analysis device 100 may simply determine whether the first lesion presence information is identical to the second lesion presence information. For example, when the first lesion presence information is 0 and the second lesion presence information is 0, the medical image analysis device 100 may make the result information 430 represent "identical." Also, when the first lesion presence information is 1 and the second lesion presence information is 1, the medical image analysis device 100 may make the result information 430 represent "identical." On the other hand, when the first lesion presence information is 0 and the second lesion presence information is 1, the medical image analysis device 100 may make the result information 430 represent "nonidentical." Also, when the first lesion presence information is 1 and the second lesion presence information is 0, the medical image analysis device 100 may make the result information 430 represent "nonidentical."

According to another embodiment of the present disclosure, the medical image analysis device 100 may perform an operation of generating result information by applying the degree of regional coincidence between first lesion area information included in first lesion information and second lesion area information included in second lesion information. This will be described with reference to FIG. 9.

Figure 9:
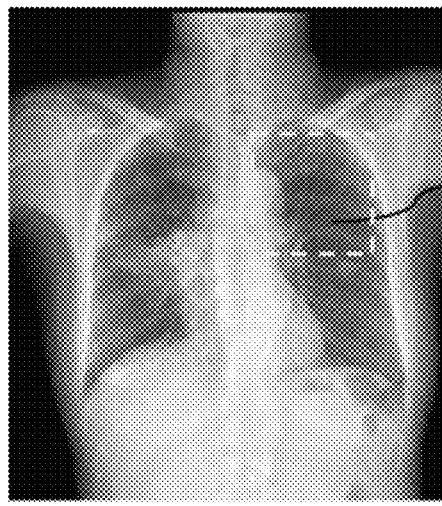
FIG. 9 is a set of images illustrating the degree of regional coincidence according to an embodiment of the present disclosure.
Figure 9:
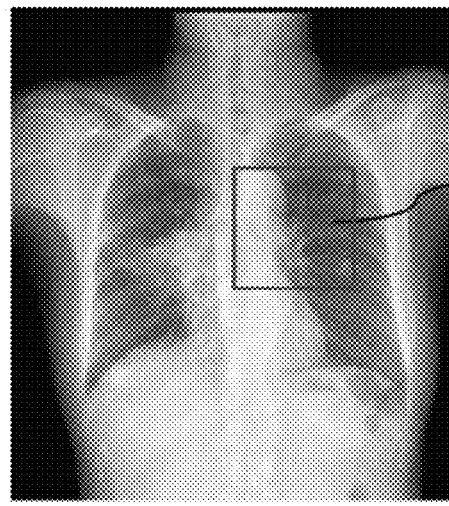
Figure 9:
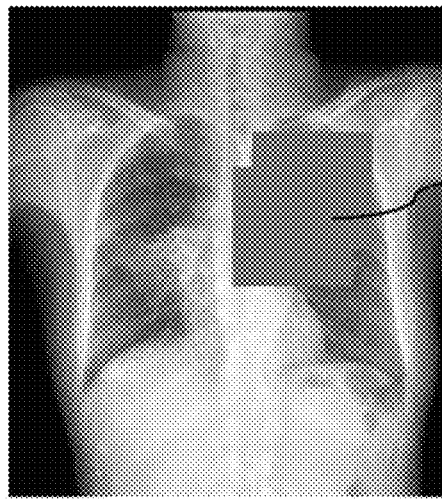
Figure 9:
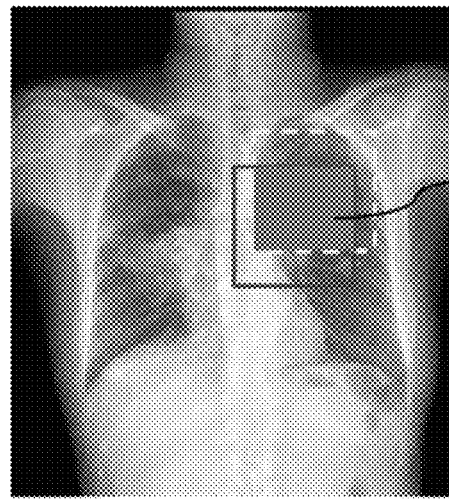

FIG. 9 is a set of images illustrating the degree of regional coincidence according to an embodiment of the present disclosure.

The medical image analysis device 100 may include the first lesion information 412 on the basis of the medical image 411. The first lesion information 412 may include first lesion area information. The first lesion area information may include information related to a size, location, or shape of a lesion. Referring to FIG. 9, the medical image analysis device 100 may determine a first lesion area 910 on the basis of the first lesion area information.

The medical image analysis device 100 may include the second lesion information 422 on the basis of the report information 421. The second lesion information 422 may include second lesion area information. The second lesion area information may include information related to a size, location, or shape of a lesion. Referring to FIG. 9, the medical image analysis device 100 may determine a second lesion area 920 on the basis of the second lesion area information.

According to an embodiment of the present disclosure, the degree of regional coincidence may be determined by the intersection over union (IOU) metric or the like. Also, the medical image analysis device 100 may acquire the result information 430 on the basis of the degree of regional coincidence without the third analysis model 400. The degree of regional coincidence represents how much two different areas overlap. On the basis of the degree of regional coincidence, the medical image analysis device 100 may determine the result information 430 to be close to 1 when the first lesion area 910 is more identical to the second lesion area 920, and may determine the result information 430 to be close to 0 when the first lesion area 910 is less identical to the second lesion area 920.

The medical image analysis device 100 may generate the result information on the basis of a union area 930 and an intersection area 940 of the first lesion area 910 and the second lesion area 920. For example, the medical image analysis device 100 may generate the result information 430 by Equation 1.

Result information=(intersection area 940 of first lesion area information and second lesion area information)/(union area 930 of first lesion area information and second lesion area information) [Equation 1]

However, the result information 430 is not only generated by Equation 1 as described above. According to another embodiment of the present disclosure, the medical image analysis device 100 may acquire result information by applying first lesion area information and second lesion area information to the third analysis model 400 which is a machine learning model. The result information may represent information on correspondence.

The third analysis model 400 may be a model which has machine-learned first past lesion area information, second past lesion area information, and information on past correspondence. The information on past correspondence may be a value input to the medical image analysis device 100 by a user on the basis of the first past lesion area information and the second past lesion area information. Alternatively, the information on past correspondence may be a value acquired by Equation 1.

The third analysis model 400 may receive first lesion area information and second lesion area information and output result information representing information on correspondence.

Referring back to FIG. 8, the medical image analysis device 100 may perform an operation of generating the result information 430 by applying the first feature information included in the first lesion information 412 and the second feature information included in the second lesion information 422 to the third analysis model 400 which is a machine learning model.

The first feature information has been described in FIGS. 5 and 6. The medical image analysis device 100 may acquire first lesion presence information by applying the medical image 411 to the first analysis model 410. When applying the medical image 411 to the first analysis model 410, the medical image analysis device 100 may determine immediately preceding values of the first lesion presence information as first feature information. The first feature information may be values included in the hidden layer of the first analysis model 410.

The second feature information has been described in FIGS. 5 and 7. The medical image analysis device 100 may acquire second lesion presence information by applying the report information 421 to the second analysis model 420. When applying the report information 421 to the second analysis model 420, the medical image analysis device 100 may determine immediately preceding values of the second lesion presence information as second feature information. The second feature information may be values included in the hidden layer of the second analysis model 420.

Referring to FIG. 8, the third analysis model 400 may be a model which has machine-learned the first past feature information included in the plurality of pieces of first past lesion information 811, the second past feature information included in the plurality of pieces of second past lesion information 812, and information related to correspondence between the first past feature information and the second past feature information included in the past result information 813.

The third analysis model 400 may receive the first feature information included in the first lesion information 412 and the second feature information included in the second lesion information 422 as inputs. The third analysis model 400 may output the result information 430 representing correspondence between the first feature information and second feature information.

According to another embodiment of the present disclosure, first lesion information may include first report information. The medical image analysis device 100 may perform an operation of generating result information by applying first report information, which is generated as a report from first lesion information, and report information to the third analysis model 400 which is a machine teaming model.

Referring to FIG. 6, the medical image analysis device 100 may acquire the first report information as the first lesion information 412 by applying the medical image 411 to the first analysis model 410. The first report information may be reports automatically acquired on the basis of the medical image 411.

Referring to FIG. 7, the medical image analysis device 100 may not include the second analysis model 420. The medical image analysis device 100 may input the report information 421 to the third analysis model 400 as it is. In other words, the second lesion information 422 may include the report information 421.

Referring to FIG. 8, the third analysis model 400 may be a model which has machine-learned first past report information included in the plurality of pieces of first past lesion information 811, past report information included in the plurality of pieces of second past lesion information 812, and information related to correspondence between the first past report information and the past report information included in the past result information 813.

The third analysis model 400 may receive the first report information included in the first lesion information 412 and the report information 421 included in the second lesion information 422 as inputs. The third analysis model 400 may output the result information 430 representing correspondence between the first report information and the report information 421.

According to another embodiment of the present disclosure, the medical image analysis device 100 may perform an operation of generating result information by applying a medical image and second lesion area information included in second lesion information to a third analysis model which is a machine learning model.

Referring to FIG. 6, the medical image analysis device 100 may not include the first analysis model 410. The medical image analysis device 100 may input the medical image 411 to the third analysis model 400 as it is. In other words, the first lesion information 412 may include the medical image 411.

Referring to FIG. 7, the medical image analysis device 100 may acquire second lesion area information as the second lesion information 422 by applying the report information 421 to the second analysis model 420. The second lesion area information may be information automatically acquired on the basis of the report information 421.

Referring to FIG. 8, the third analysis model 400 may be a model which has machine-learned past medical images included in the plurality of pieces of first past lesion information 811, second past lesion area information included in the plurality of pieces of second past lesion information 812, and information related to correspondence, which is included in the past result information 813, between the past medical images and the second past lesion area information.

The third analysis model 400 may receive the medical image 411 and the second lesion area information included in the second lesion information 422 as inputs. The third analysis model 400 may output the result information 430 representing correspondence between first report information and the report information 421.

Figure 10:
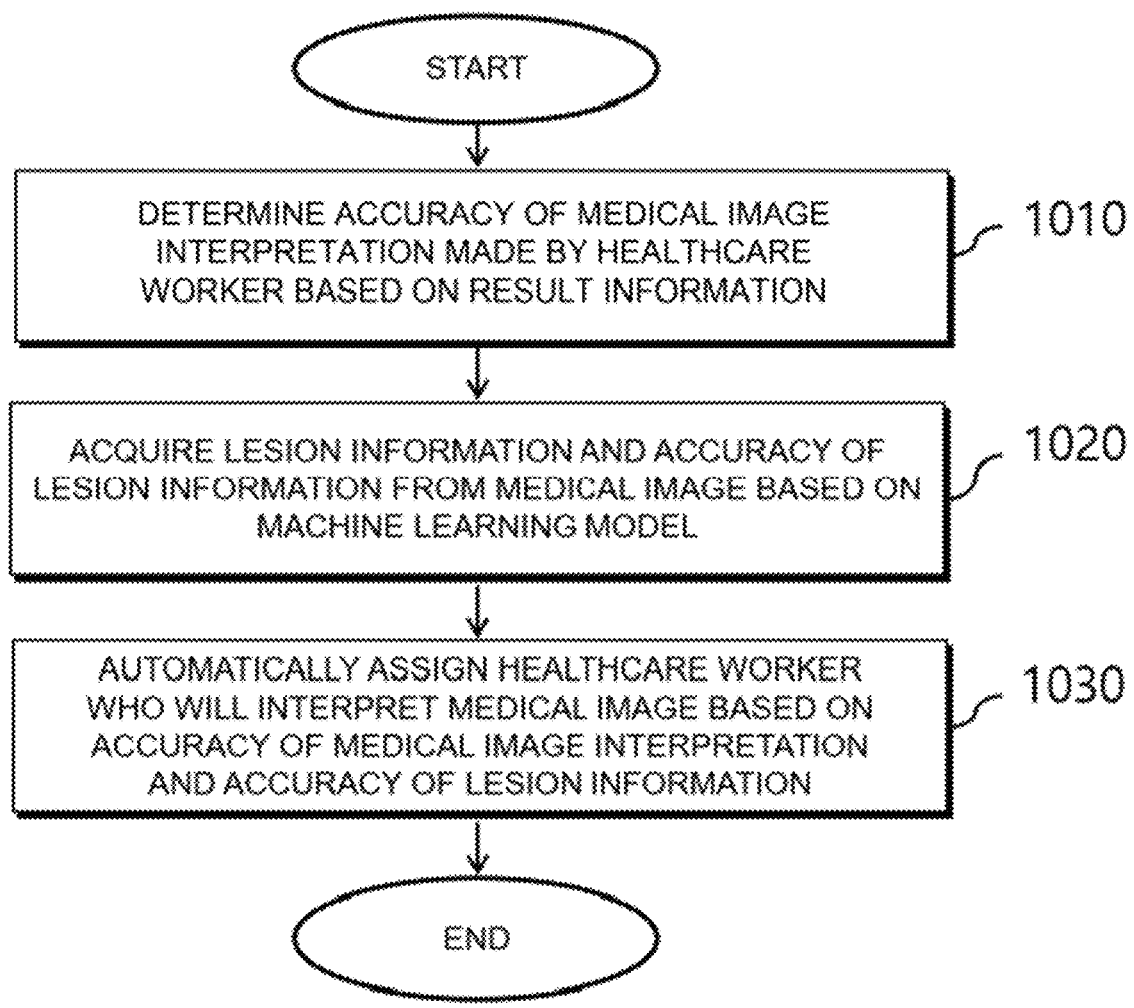
FIG. 10 is a flowchart illustrating an operation of a medical image analysis device according to an embodiment of the present disclosure.

FIG. 10 is a flowchart illustrating an operation of a medical image analysis device according to an embodiment of the present disclosure.

The medical image analysis device 100 may perform an operation 1010 of determining the accuracy of a medical image interpretation made by a healthcare worker on the basis of the result information 430. Referring to FIG. 4, the first lesion information 412 may represent diagnosis results which have been automatically generated regarding the medical image 411 by the medical image analysis device 100. Also, the second lesion information 422 may represent diagnosis results generated regarding the medical image 411 by a healthcare worker. The result information 430 may represent correspondence between the first lesion information 412 and the second lesion information 422. The medical image analysis device 100 may cumulatively store result information of healthcare workers. When the reliability of the first lesion information 412 is high, the medical image analysis device 100 may determine the accuracy of the medical image interpretation of the healthcare worker on the basis of the result information 430. In other words, since it is possible to rely on the first lesion information 412, the accuracy of the medical image interpretation of the healthcare worker is determined on the basis of the first lesion information 412.

Specifically, the accuracy of the medical image interpretation of the healthcare worker may be based on the number of times that the first lesion information 412 is identical to the second lesion information 422. Also, the accuracy of the medical image interpretation of the healthcare worker may be based on a ratio of the number of times that the first lesion information 412 is identical to the second lesion information 422 to the total number of medical image interpretation times of the healthcare worker.

However, the accuracy of the medical image interpretation of the healthcare worker is not limited thereto. An expert healthcare worker may evaluate whether the report information 421 of another healthcare worker is accurate, and the medical image analysis device 100 may receive evaluation results of the expert healthcare worker. The medical image analysis device 100 may determine the evaluation results of the expert healthcare worker as the accuracy of the medical image interpretation of the healthcare worker.

The medical image analysis device 100 may perform an operation 1020 of acquiring lesion information and the accuracy of the lesion information from the medical image on the basis of a machine learning model. The machine learning model may include the above-described first analysis model. The machine learning model may acquire the accuracy of the lesion information together with at least one of first lesion presence information, first lesion type information, first lesion area information, and first report information from the medical image. The accuracy of lesion information may vary depending on a medical image.

For example, the machine learning model may acquire the probability of a lesion in the medical image and the probability of no lesion in the medical image respectively. The machine learning model may determine the first lesion presence information on the basis of a higher probability. For example, when the probability of a lesion in the medical image is higher than the probability of no lesion in the medical image, the machine learning model may cause the first lesion information to represent that a lesion exists in the medical image.

When the difference between the probability of a lesion in the medical image and the probability of no lesion in the medical image is smaller than a certain threshold value, the machine learning model may determine that the accuracy of the lesion information is low. On the other hand, when the difference between the probability of a lesion in the medical image and the probability of no lesion in the medical image is larger than the certain threshold value, the machine learning model may determine that the accuracy of the lesion information is high.

A case in which the machine learning model acquires the first lesion presence information has been described above, but the same process may be carried out for the first lesion type information, the first lesion area information, or the first report information.

The medical image analysis device 100 may perform an operation 1030 of automatically assigning a healthcare worker who will interpret a medical image on the basis of the accuracy of medical image interpretations of healthcare workers and the accuracy of lesion information of the machine learning model. The medical image analysis device 100 may determine the accuracy of medical image interpretations made by healthcare workers by performing the operation 1010. The medical image analysis device 100 may acquire the accuracy of lesion information generated regarding medical images by the machine learning model by performing the operation 1020. The accuracy of lesion information of the machine learning model may vary depending on a medical image.

The medical image analysis device 100 may assign a medical image having lower accuracy in the lesion information of the machine learning model to a healthcare worker having higher medical image interpretation accuracy. A healthcare worker having high medical image interpretation accuracy may denote that the healthcare worker is experienced. Also, low accuracy in lesion information generated by the machine learning model may denote that it is difficult to interpret the medical image through the machine learning model. This may also denote that the medical image is a rare case. The medical image analysis device 100 may prevent malpractice by assigning a medical image which is difficult to interpret to an experienced healthcare worker.

On the other hand, the medical image analysis device 100 may assign a medical image having higher accuracy in the lesion information generated by the machine learning model to a healthcare worker having lower medical image interpretation accuracy. A healthcare worker having low medical image interpretation accuracy may denote that the healthcare worker is inexperienced. Also, high accuracy in lesion information generated by the machine learning model may denote that it is easy to interpret the medical image through the machine learning model. This may also denote that the medical image is a common case. The medical image analysis device 100 may assign a medical image which is easy to interpret to an inexperienced healthcare worker, thereby preventing malpractice and enabling the healthcare worker to experience various cases.

A process of assigning a medical image to a healthcare worker according to proficiency of the healthcare worker has been described above. However, the same process may be carried out for a hospital rather than a healthcare worker. Specifically, the medical image analysis device 100 may perform an operation 1010 of determining the medical image interpretation accuracy of a hospital on the basis of result information 430. Also, the medical image analysis device 100 may perform an operation 1020 of acquiring lesion information and the accuracy of the lesion information from medical images on the basis of a machine learning model. The medical image analysis device 100 may perform an operation 1030 of automatically assigning a hospital which will interpret a medical image on the basis of the medical image interpretation accuracy of the hospital and the accuracy of the lesion information of the machine learning model. Except that a healthcare worker is replaced by a hospital, the medical image analysis device 100 performs the same operation, and the same description will not be reiterated.

Figure 11:
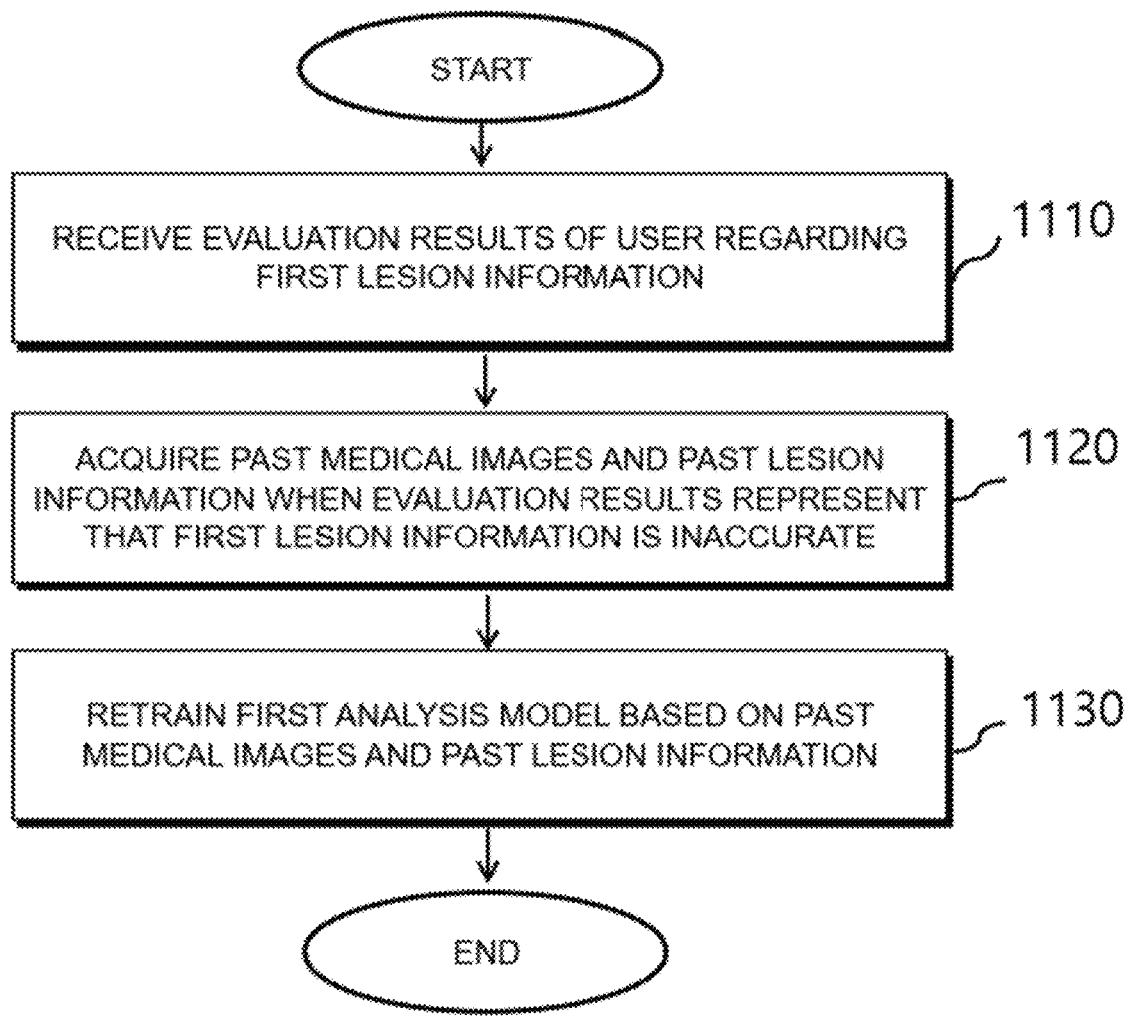
FIG. 11 is a flowchart illustrating an operation of a medical image analysis device according to an embodiment of the present disclosure.

FIG. 11 is a flowchart illustrating an operation of a medical image analysis device according to an embodiment of the present disclosure.

The medical image analysis device 100 may perform an operation 1110 of receiving evaluation results of a user regarding first lesion information 412. The user may determine whether the first lesion information 412 acquired through the first analysis model 410 is accurate or inaccurate and input the information to the medical image analysis device 100. The medical image analysis device 100 may determine whether the first lesion information 412 is accurate or inaccurate on the basis of the user's input. This process may be performed by the model evaluation unit 115 of the medical image analysis device 100.

When the evaluation results represent that the first lesion information 412 is inaccurate, the medical image analysis device 100 may perform an operation 1120 of acquiring past medical images and past lesion information. The past medical images and the past lesion information may include past medical images and past lesion information which are updated in order to update the first analysis model 410. The medical image analysis device 100 may perform the operation 1120 using the model update unit 125.

The medical image analysis device 100 may perform an operation 1130 of retraining the first analysis model 410 on the basis of the past medical images and the past lesion information. The medical image analysis device 100 may store the retrained first analysis model 410 in the memory or transmit the retrained first analysis model 410 to another medical image analysis device. The retrained first analysis model 410 may derive a lesion from a medical image more accurately and more rapidly than the existing first analysis model 410. Retraining may denote additional learning or continual learning. The medical image analysis device 100 according to an embodiment of the present disclosure may constantly improve the first analysis model 410, thereby supporting medical image interpretation of healthcare workers.

Figure 12:
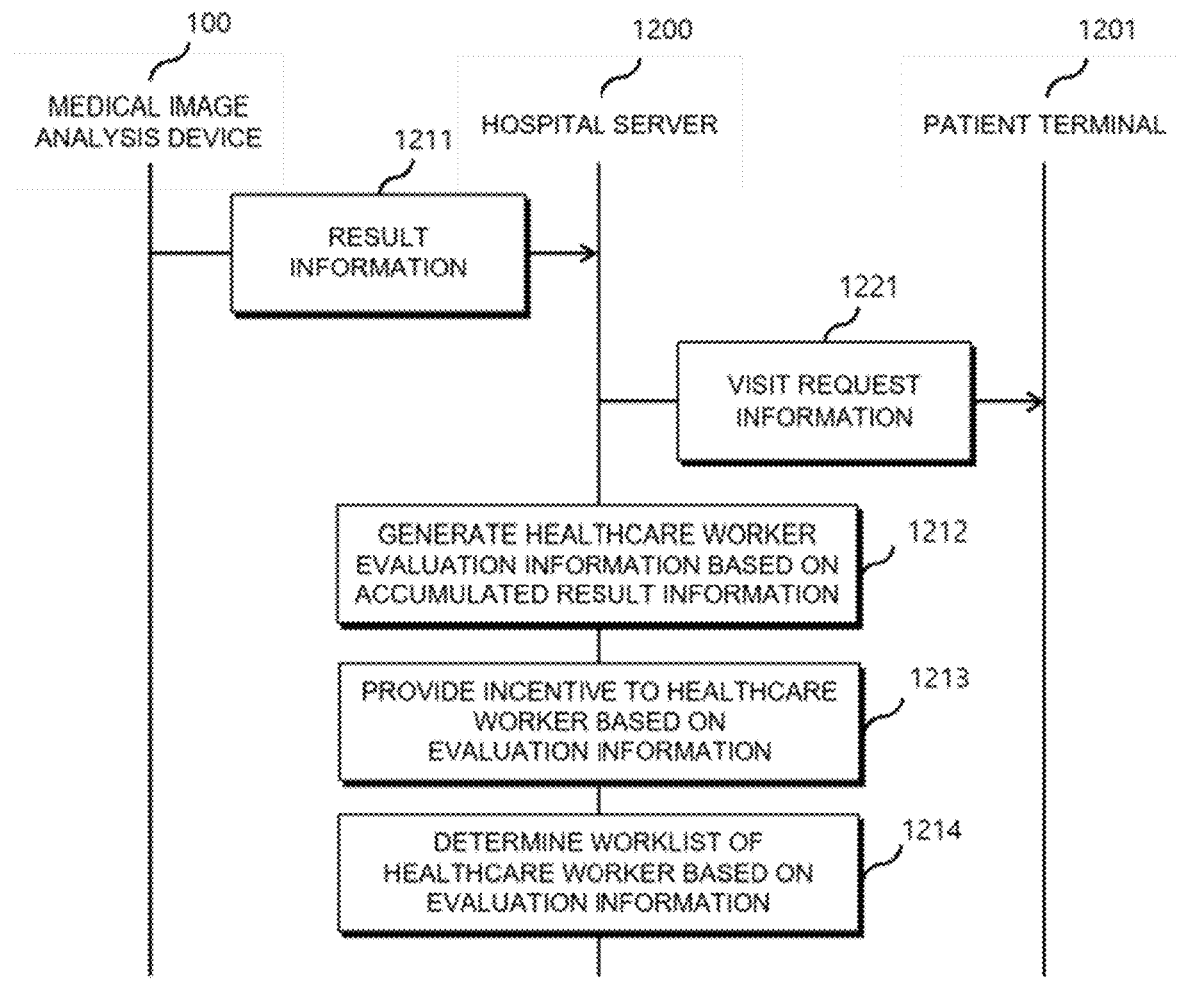
FIG. 12 is a sequence diagram illustrating an operation of a medical image analysis system according to an embodiment of the present disclosure.

FIG. 12 is a sequence diagram illustrating an operation of a medical image analysis system according to an embodiment of the present disclosure.

The medical image analysis system may include at least one of a medical image analysis device 100, a hospital server 1200, a patient terminal 1201, a terminal of a healthcare worker, and a payer server. The payer server may include at least one of an insurance company server, a National Health Insurance Service server, and a Center for Medicare and Medicaid Service (CMS) server.

A healthcare worker may diagnose a patient and generate report information 421. The medical image analysis device 100 may determine the accuracy of the report information 421 of the healthcare worker as follows.

The medical image analysis device 100 may cumulatively store result information 430 in the memory. The medical image analysis device 100 may perform an operation 1211 of transmitting the result information 430 to the hospital server 1200. The result information 430 may include information on correspondence between first lesion information 412 and second lesion information 422. When it is determined that the first lesion information 412 differs from the second lesion information 422 on the basis of the result information 430, the hospital server 1200 may determine which one of the first lesion information 412 and the second lesion information 422 is inaccurate.

The medical image analysis device 100 may acquire the accuracy of the first lesion information 412 from the first analysis model 410. The accuracy may be determined on the basis of how much the probability of the first lesion information 412 derived by applying a medical image 411 to the first analysis model 410 is higher than the probabilities of other pieces of lesion information which may be derived by the first analysis model 410. This has been already described in FIG. 10, and the same description will not be reiterated.

When the accuracy of the first lesion information 412 is high and the first lesion information 412 differs from the second lesion information 422, the hospital server 1200 may determine that the second lesion information 422 is inaccurate. Also, the medical image analysis device 100 may determine that the second lesion information 422 is inaccurate on the basis of a user's input. The second lesion information 422 being inaccurate may denote that there is information included in the first lesion information 412 but the information is not included in the second lesion information 422, or there is information included in the second lesion information 422 but the information is not included in the first lesion information 412.

When the second lesion information 422 is inaccurate, the hospital server 1200 may generate visit request information. The visit request information may include at least one of the result information 430 and the first lesion information 412. The hospital server 1200 may perform an operation 1221 of transmitting the visit request information to the patient terminal 1201 to request the patient for a medical checkup again. The patient may get information displayed in the patient terminal 1201 and go to the hospital. The visit request information may include at least one of the result information 430 and the first lesion information 412. However, the visit request information is not limited thereto, and a user may request the patient for a visit by mail or e-mail according to the visit request information displayed by the hospital server 1200.

When the second lesion information 422 is inaccurate, the medical image analysis device 100 rather than the hospital server 1200 may generate the visit request information. Then, the medical image analysis device 100 may transmit the visit request information to the patient terminal 1201 or the hospital server 1200.

Also, the hospital server 1200 or the medical image analysis device 100 may transmit the visit request information to a doctor's terminal or an insurance company server in addition to the patient terminal 1201. The hospital server 1200 may determine at least one of schedule information of a medical re-checkup for the patient, a processing flow in the hospital, and a patient worklist on the basis of the visit request information.

The hospital server 1200 may cumulatively store the result information 430 in the memory. The hospital server 1200 may perform an operation 1212 of generating evaluation information of a healthcare worker belonging to the hospital on the basis of the accumulated result information. For example, the hospital server 1200 may acquire the report information 421 of the healthcare worker or the second lesion information 422. The hospital server 1200 may generate evaluation information of the healthcare worker on the basis of the number of times that the report information 421 or the second lesion information 422 of the healthcare worker is identical to first lesion information. Alternatively, an experienced healthcare worker may input evaluation information to the hospital server 1200 on the basis of the report information 421 or the second lesion information 422 of the healthcare worker. The hospital server 1200 may determine evaluation information of the healthcare worker on the basis of the experienced healthcare worker's input.

The hospital server 1200 may perform an operation 1213 of providing an incentive to the healthcare worker on the basis of the evaluation information. For example, the hospital server 1200 may provide an incentive to the healthcare worker in conjunction with a healthcare worker salary server when the evaluation information is favorable. On the other hand, when the evaluation information is unfavorable, the hospital server 1200 may suggest a manager that the healthcare worker is given a penalty or attends retraining.

The hospital server 1200 may perform an operation 1214 of determining a patient worklist of the healthcare worker on the basis of the evaluation information. For example, the hospital server 1200 may determine a patient worklist so that a healthcare worker having favorable evaluation information may take charge of an emergency patient who is difficult to take care of. Also, the hospital server 1200 may determine a patient worklist so that a healthcare worker having unfavorable evaluation information may take charge of a patient who is easy to take care of.

Figure 13:
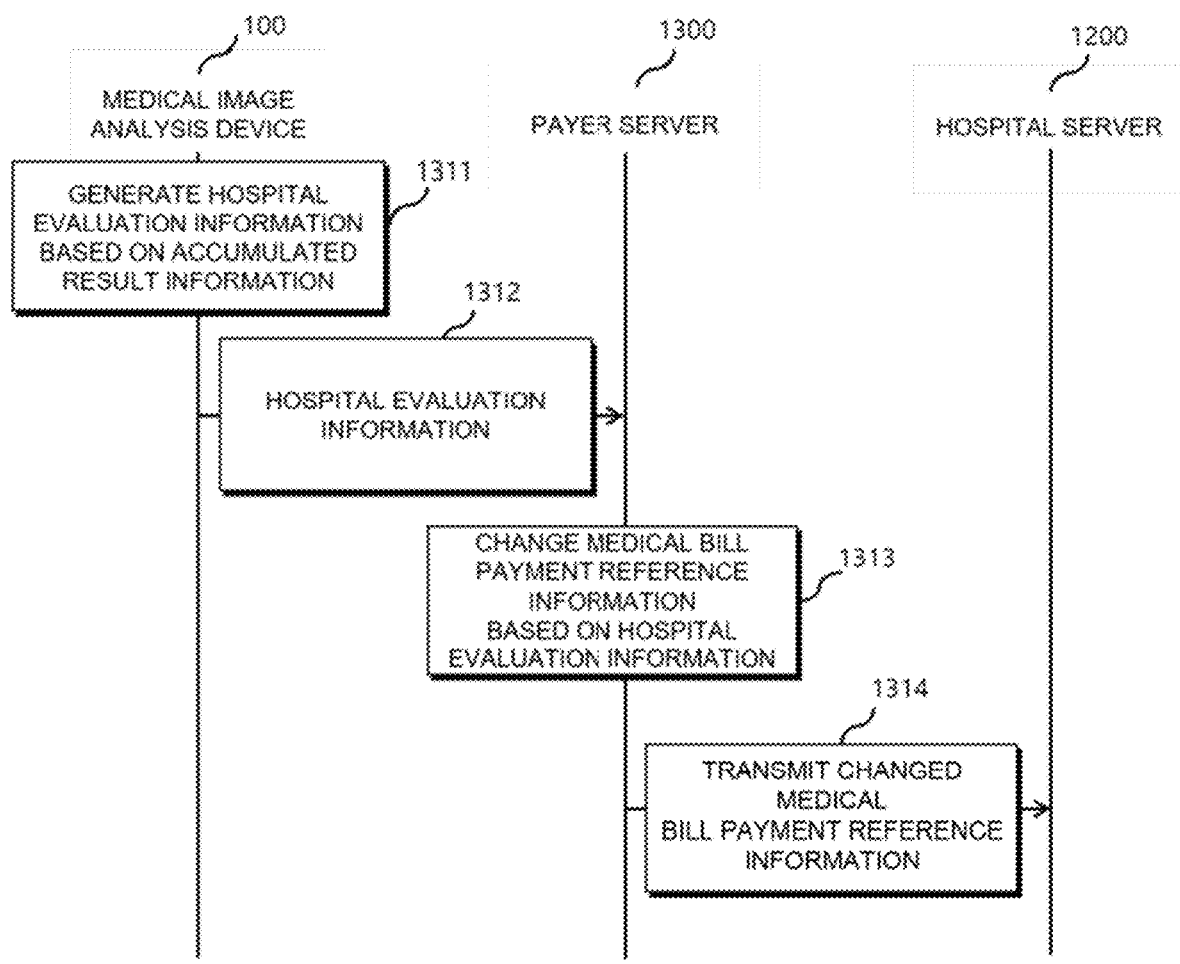
FIG. 13 is a sequence diagram illustrating an operation of a medical image analysis system according to an embodiment of the present disclosure.

FIG. 13 is a sequence diagram illustrating an operation of a medical image analysis system according to an embodiment of the present disclosure.

The medical image analysis device 100 may cumulatively store result information 430 in the memory. The medical image analysis device 100 may perform an operation 1311 of generating hospital evaluation information on the basis of the accumulated result information. The hospital evaluation information may represent a ratio at which healthcare workers belonging to the hospital have accurately interpreted medical images. The hospital evaluation information may be acquired on the basis of a ratio of a number of times that first lesion information 412 is identical to second lesion information 422 to a total number of interpretations made by healthcare workers of the hospital. The number of times that the first lesion information 412 is identical to the second lesion information 422 may be acquired on the basis of the third analysis model 400. As described above, the first lesion information 412 is lesion information acquired by interpreting a medical image on the basis of the first analysis model 410, and the second lesion information 422 is lesion information acquired by applying the second analysis model 420 to report information of a healthcare worker. When the first lesion information 412 is identical to the second lesion information 422, the medical image analysis device 100 may determine that the healthcare worker has accurately interpreted the medical image.

Also, the medical image analysis device 100 may receive hospital evaluation information from an experienced healthcare worker and determine hospital evaluation information. When first lesion information is identical to second lesion information, the medical image analysis device 100 may determine that the healthcare worker has accurately interpreted the medical image.

When first lesion information differs from second lesion information, the experienced healthcare worker may select inaccurate information between the first lesion information and the second lesion information. When the first lesion information is inaccurate, the medical image analysis device 100 may update the first analysis model 410. The medical image analysis device 100 may update the first analysis model 410 in the same way as described in FIG. 6. The medical image analysis device 100 may update the first analysis model 410 on the basis of a plurality of past medical images 611 and a plurality of pieces of first past lesion information 612. The medical image analysis device 100 may use the plurality of past medical images 611 and the plurality of pieces of first past lesion information 612 as ground truth information. Also, the first past lesion information 612 may further include second lesion information which has been determined to be accurate information by an experienced healthcare worker.

When the second lesion information is inaccurate, the medical image analysis device 100 may determine hospital evaluation information on the basis of the number of times that the first lesion information is identical to the second lesion information in relation to a total number of interpretations made by healthcare workers. The number of times that the first lesion information 412 is identical to the second lesion information 422 may be acquired on the basis of the third analysis model 400.

The medical image analysis device 100 may provide hospital evaluation information of each hospital. Also, the medical image analysis device 100 may provide information on the average of overall hospital evaluation information. Further, the medical image analysis device 100 may provide information on the average of local hospital evaluation information. Patients may retrieve the statistical data of hospital evaluation information from the medical image analysis device 100. Since patients are able to select a hospital on the basis of objective information, high quality service may be provided. Also, since hospitals are going to work hard to improve their evaluation information, overall service quality may be improved.

The medical image analysis device 100 may provide various types of statistical data of hospitals. The medical image analysis device 100 may provide information on the modality-specific numbers of interpretations made in a hospital. For example, the medical image analysis device 100 may provide information on the number of times that healthcare workers of a hospital have interpreted ultrasonic images, CT images, MR images, or the like. Patients may estimate proficiency of the healthcare workers of the hospital on the basis of the modality-specific numbers of interpretations.

The medical image analysis device 100 may provide information related the number of times that healthcare workers belonging to a hospital have interpreted medical images as normal or abnormal. An interpretation as normal may denote that there is no lesion in the medical image, and an interpretation as abnormal may denote that there is a lesion in the medical image.

The medical image analysis device 100 may provide information on the accuracy of medical image interpretations made by healthcare workers belonging to a hospital. For example, the medical image analysis device 100 may determine information on the accuracy on the basis of a ratio of the number of times that lesion information interpreted by a healthcare worker differs from lesion information interpreted by the first analysis model 410 to a total number of medical image interpretations made by the healthcare workers belonging to the hospital. The medical image analysis device 100 may determine whether lesion information interpreted by a healthcare worker differs from lesion information interpreted by the first analysis model 410 using the third analysis model 400.

The medical image analysis device 100 may transmit the hospital evaluation information to an external server. The external server may provide the result information or the hospital evaluation information in a website format. A user may retrieve the hospital evaluation information using a web browser. Also, the medical image analysis device 100 may transmit the hospital evaluation information to a user terminal. A user may easily retrieve hospital evaluation information of a hospital that he or she will use or used in the past using his or her terminal.

The medical image analysis device 100 may perform an operation 1312 of transmitting the hospital evaluation information to a payer server 1300. The payer server 1300 may denote a server corresponding to a subject which pays a medical bill and include, for example, at least one of an insurance company server, a National Health Insurance Service server, and a CMS server.

The payer server 1300 may perform an operation 1313 of changing medical bill payment reference information on the basis of the hospital evaluation information. For example, the payer server 1300 may change the medical bill payment reference information so that a hospital having better hospital evaluation information may charge a higher medical bill. Also, the payer server 1300 may change the medical bill payment reference information so that a hospital having worse hospital evaluation information may charge a lower medical bill. However, the medical bill payment reference information is not limited thereto. The payer server 1300 may change the medical bill payment reference information so that a hospital having better hospital evaluation information may charge a lower medical bill and may change the medical bill payment reference information so that a hospital having worse hospital evaluation information may charge a higher medical bill. The payer server 1300 may generate information for charging a lower medical bill in a hospital having better hospital evaluation information but inducing many patients to go to the hospital.

The payer server 1300 may perform an operation 1314 of transmitting the changed medical bill payment reference information to the hospital server 1200, an external server, or a user terminal. Also, a manager of a hospital may make an effort to improve the accuracy of medical image interpretations made in the hospital on the basis of the medical bill payment reference information displayed in the hospital server 1200.

The external server may provide the received medical bill payment reference information to users in a website format. Users may retrieve medical bill payment reference information of hospitals that they will use or have used in the past.

The user terminal may display the received medical bill payment reference information. The user may easily retrieve the medical bill payment reference information using the terminal.

The medical image analysis device 100 according to an embodiment of the present disclosure has been described above. The medical image analysis device 100 according to an embodiment of the present disclosure may compare a medical image interpretation by a machine learning model with a medical image interpretation by a healthcare worker. Consequently, it is possible to improve the accuracy of a medical image interpretation. Also, while it is difficult in practice for a plurality of healthcare workers to interpret one medical image in terms of time and cost, the medical image analysis device 100 according to an embodiment of the present disclosure interprets a medical image which has been already interpreted by a healthcare worker again using a machine learning model and thus can reduce omission of lesion information which may occur in a medical image interpretation. Further, the medical image analysis device 100 according to an embodiment of the present disclosure makes it possible to improve medical service and reduce medical costs by detecting a lesion in the early stage. In addition, the medical image analysis device 100 according to an embodiment may improve the performance of a machine learning model.

Meanwhile, the above-described embodiments of the present disclosure can be written as a program that can be executed in a computer and can be implemented by a general-use digital computer which runs the program using computer-readable recording media. The computer-readable recording media include storage media, such as magnetic storage media (e.g., a ROM, a floppy disk, and a hard disk) and optical media (e.g., a compact disc (CD)-ROM and a digital versatile disc (DVD)).

Various embodiments of the present disclosure have been described above. Those of ordinary skill in the art will appreciate that various modifications and equivalents can be made from embodiments without departing from the essential characteristics of the present disclosure. Therefore, the above-described embodiments should be construed as illustrative rather than limiting. The scope of the present disclosure is defined by the claims rather than the above description, and all differences within the equivalency range of the claims should be construed as falling within the scope of the present disclosure.

What is claimed is:

1. A computerized image interpretation method comprising:
   receiving, at a medical image analysis device comprising at least one processor, a medical image;
   processing the medical image, at the medical image analysis device and using a first analysis model, to obtain first lesion information representing one or more lesions in the medical image, wherein the first analysis model is machine-trained based on correlation between a plurality of training medical images and first past lesion information representing lesions contained in the plurality of training medical images;
   receiving, at the medical image analysis device, report information comprising a healthcare worker's judgement result of the medical image;
   processing the report information, at the medical image analysis device and using a second analysis model different from the first analysis model, to obtain second lesion information representing one or more lesions in the medical image;
   processing the first lesion information and the second lesion information, at the medical image analysis device and using a third analysis model different from the first and second analysis models, to generate result information representing a correspondence between the first lesion information and the second lesion information, wherein the third analysis model is machine-trained based on correlation between a plurality of training first past lesion information and second past lesion information; and
   outputting, at the medical image analysis device, the result information,
   wherein the first lesion information includes first lesion area information, wherein the second lesion information comprises second lesion area information, wherein each of the first lesion area information and the second lesion area information comprises information related to at least one of a size, location, or shape of a lesion, wherein a first lesion area is determined, at the medical analysis device, based on the first lesion area information and a second lesion area is determined, at the medical analysis device, based on the second lesion area information, and wherein the medical image analysis device obtains the result information based on how much the first lesion area and the second lesion area overlap.

2. The image interpretation method of claim 1, wherein the first lesion information includes first feature information about at least one feature related to a hidden layer of the first analysis model.

3. The image interpretation method of claim 1, wherein the method further comprises:

determining, at the medical image analysis device, a combined area of the first and second lesion areas;

determining, at the medical image analysis device, an overlapping area of the first and second lesion areas; and obtaining, at the medical image analysis device, the result information based on a ratio of the overlapping area and the combined area.

4. The image interpretation method of claim 1, wherein the second analysis model is machine-trained based on correlation between a plurality of training report information and the second past lesion information representing lesions contained in the plurality of training report information and wherein the second lesion information includes second feature information about at least one feature related to a hidden layer of the second analysis model.

5. The image interpretation method of claim 1, wherein the second analysis model comprises a rule-based model for extracting the second lesion information from the report information.

6. The image interpretation method of claim 1, further comprising transmitting the result information to a healthcare provider server such that healthcare worker evaluation information is generated based on accumulated result information.

7. The image interpretation method of claim 1, further comprising transmitting the result information to a healthcare provider server such that a patient worklist is generated based on the result information.

8. A device for analyzing a medical image, the device comprising a memory storing computer-executable instructions and a processor configured to executed the computer-executable instructions and, wherein the processor is configured, by executing the computer-executable instructions, to perform:

receiving a medical image;

processing the medical image, at the medical image analysis device and using a first analysis model, to obtain first lesion information representing one or more lesions in the medical image, wherein the first analysis model is machine-trained based on correlation between a plurality of training medical images and first past lesion information representing lesions contained in the plurality of training medical images;

receiving report information comprising a healthcare worker's judgement result of the medical image;

processing the report information, using a second analysis model different from the first analysis model, to obtain second lesion information representing one or more lesions in the medical image;

processing the first lesion information and the second lesion information, using a third analysis model different from the first and second analysis models, to generate result information representing a correspondence between the first lesion information and the second lesion information, wherein the third analysis model is machine-trained based on correlation between a plurality of training first past lesion information and second past lesion information; and outputting, at the medical image analysis device, the result information, wherein the first lesion information includes first lesion area information, wherein the second lesion information comprises second lesion area information, wherein each of the first lesion area information and the second lesion area information comprises information related to at least one of a size, location, or shape of a lesion, wherein a first lesion area is determined, at the medical analysis device, based on the first lesion area information and a second lesion area is determined, at the medical analysis device, based on the second lesion area information, and wherein the medical image analysis device obtains the result information based on how much the first lesion area and the second lesion area overlap.

9. The device of claim 8, wherein the first lesion information includes first feature information a t least one feature related to a hidden layer of the first analysis model.

10. The device of claim 8, wherein the method further comprises:

determining, at the medical image analysis device, a combined area of the first and second lesion areas;

determining, at the medical image analysis device, an overlapping area of the first and second lesion areas; and obtaining, at the medical image analysis device, the result information based on a ratio of the overlapping area and the combined area.

11. The device of claim 8, wherein the second analysis model is machine-trained based on correlation between a plurality of training report information and the second past lesion information representing lesions contained in the plurality of training report information and wherein the second lesion information includes second feature information about at least one feature related to a hidden layer of the second analysis model.

12. The device of claim 8, wherein the second analysis model comprises a rule-based model for extracting the second lesion information from the report information.

* * * * *

UNITED STATES PATENT AND TRADEMARK OFFICE
CERTIFICATE OF CORRECTION

PATENT NO. : 10,825,178 B1
APPLICATION NO. : 16/707830
DATED : November 3, 2020
INVENTOR(S) : Nayoung Jeong, Ki Hwan Kim and Minhong Jang It is certified that error appears in the above-identified patent and that said Letters Patent is hereby corrected as shown below:

In the Specification

In Column 6 at Line 63, delete "*teaming*" and insert --*learning*--.

In Column 8 at Line 28, delete "*teaming*" and insert --*learning*--.

In Column 8 at Line 34, change "*bidirectional*" to --*bi-directional*--.

In Column 9 at Line 31, delete "*teaming*" and insert --*learning*--.

In Column 10 at Line 40, delete "*teaming*" and insert --*learning*--.

In Column 17 at Line 61, delete "*teaming*" and insert --*learning*--.

In Column 18 at Line 6, delete "*teaming*" and insert --*learning*--.

In Column 21 at Line 3, change "*FIG. together*" to --*FIG. 1 together*--.

In Column 21 at Line 15-16, change "*computer readable*" to --*computer-readable*--.

In Column 23 at Line 24, delete "*teaming*" and insert --*learning*--.

In Column 26 at Line 11, delete "*teaming*" and insert --*learning*--.

In Column 32 at Line 46, change "*MR*" to --*MRI*--.

Signed and Sealed this
Second Day of March, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,825,178 B1

In the Claims

In Column 35 at Line 49, Claim 9, change "*executed*" to --*execute*--.

In Column 36 at Line 36, Claim 9, change "*a t least*" to --*about at least*--.